US012661324B2

(12) United States Patent
Lin et al.

(10) Patent No.: US 12,661,324 B2
(45) Date of Patent: Jun. 23, 2026

(54) SOLID DISPERSION, PHARMACEUTICAL PREPARATIONS, PREPARATION METHOD, AND APPLICATION THEREOF

(71) Applicants: ASCENTAGE PHARMA (SUZHOU) CO., LTD., Suzhou (CN); ASCENTAGE PHARMA GROUP CORP LIMITED, Admiralty (HK)

(72) Inventors: Yanqiong Lin, Suzhou (CN); Hualiang Xu, Suzhou (CN); Feng Xu, Suzhou (CN); Chen Wu, Suzhou (CN); Hongtao Guo, Suzhou (CN); Xiaoling He, Suzhou (CN)

(73) Assignees: ASCENTAGE PHARMA (SUZHOU) CO., LTD., Suzhou (CN); ASCENTAGE PHARMA GROUP CORP LIMITED, Hong Kong (CN)

( * ) Notice: Subject to any disclaimer, the term of this patent is extended or adjusted under 35 U.S.C. 154(b) by 397 days.

(21) Appl. No.: 18/038,628

(22) PCT Filed: Nov. 25, 2021

(86) PCT No.: PCT/CN2021/132990
§ 371 (c)(1),
(2) Date: May 24, 2023

(87) PCT Pub. No.: WO2022/111558
PCT Pub. Date: Jun. 2, 2022

(65) Prior Publication Data

US 2024/0016747 A1 Jan. 18, 2024

(30) Foreign Application Priority Data

Nov. 25, 2020 (CN) ......................... 202011343661.6
Nov. 25, 2020 (WO) ................ PCT/CN2020/131357

(51) Int. Cl.

| | |
|---|---|
| ***A61K 9/28*** | (2006.01) |
| ***A61K 9/14*** | (2006.01) |
| ***A61K 31/635*** | (2006.01) |
| ***A61K 47/02*** | (2006.01) |
| ***A61K 47/10*** | (2017.01) |
| ***A61K 47/26*** | (2006.01) |
| ***A61K 47/32*** | (2006.01) |
| ***A61K 47/38*** | (2006.01) |

(52) U.S. Cl.
CPC ............ *A61K 9/2866* (2013.01); *A61K 9/146* (2013.01); *A61K 31/635* (2013.01); *A61K 47/02* (2013.01); *A61K 47/10* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

2017/0189426 A1 7/2017 Packhaeuser et al.

FOREIGN PATENT DOCUMENTS

| | | | | |
|---|---|---|---|---|
| CN | 103167867 A | 6/2013 | | |
| CN | 103282025 A | 9/2013 | | |
| CN | 107648185 A | 2/2018 | | |
| CN | 111537654 B | 11/2020 | | |
| EP | 3333167 A1 * | 6/2018 | ........... | C07D 471/04 |
| JP | 2012-529490 A | 11/2012 | | |
| JP | 2013-544804 A | 12/2013 | | |

(Continued)

OTHER PUBLICATIONS

Extended EP Search Report, dated Sep. 16, 2024 and issued in connection with European Patent Application No. 21897058.0, 13 pages.

(Continued)

*Primary Examiner* — Melissa S Mercier
(74) *Attorney, Agent, or Firm* — Barnes & Thornburg LLP; Ryan L. Marshall

(57) ABSTRACT

The invention discloses a solid dispersion, a pharmaceutical preparation, a preparation method and an application thereof. The solid dispersion of the invention comprises carriers and active constituents, which is a compound as shown in formula (I) and/or a pharmaceutically acceptable salt thereof; The carrier is "homopolymer and copolymer of N-vinyl lactam" and/or pH-dependent cellulose derivatives. The preparation of the invention comprises the solid dispersion, fillers and disintegrating agents. The solid dispersion of the invention has good dissolution and significantly improves the solubility of effective constituents. The preparation can effectively improve the bioavailability of Bcl-2 inhibitor, has good dissolution and stability, and can improve the safety of a medication.

(I)

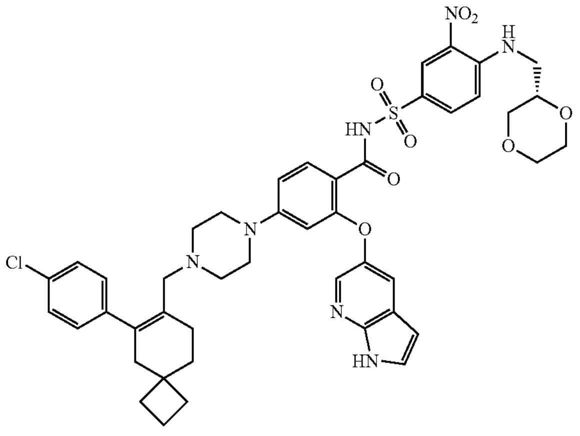

16 Claims, 4 Drawing Sheets

(56) References Cited

FOREIGN PATENT DOCUMENTS

| | | | | | |
|---|---|---|---|---|---|
| JP | 2019-521110 | A | | 7/2019 | |
| JP | 2019-527705 | A | | 10/2019 | |
| WO | WO-2018027097 | A1 | * | 2/2018 | ............. A61P 35/02 |
| WO | 2020024820 | A1 | | 2/2020 | |
| WO | 2020103921 | A1 | | 5/2020 | |

OTHER PUBLICATIONS

International Search Report dated Feb. 22, 2022, prepared in International Application No. PCT/CN2021/132990.
Written Opinion of the ISA dated Feb. 17, 2022, prepared in International Application No. PCT/CN2021/132990.
English translation of Japanese Office Action mailed Jul. 18, 2025 and issued in connection with JP Appln. No. 2023-532648.

* cited by examiner

SOLID DISPERSION, PHARMACEUTICAL PREPARATIONS, PREPARATION METHOD, AND APPLICATION THEREOF

CROSS REFERENCE TO RELATED APPLICATIONS

This application is a National Stage application of International Application No. PCT/CN2021/132990, filed Nov. 25, 2021. This application also claims the benefit of priority under 35 U.S.C. § 119 to International Patent Application No. PCT/CN2020/131357, filed Nov. 25, 2020, and Chinese Application No. 202011343661.6, filed Nov. 25, 2020, each of which is incorporated by reference herein in its entirety for any purpose.

TECHNICAL FIELD

The invention relates to a solid dispersion, a pharmaceutical preparation, a preparation method and an application thereof.

BACKGROUND ART

The compound 4-{4-{[6-(4-Chloro-phenyl)-spiro[3,5] nonane-6-ene-7-yl] methyl}-piperazine-1-yl}-N-{{3-nitro-4-[((2S)-[1,4]dioxane-2-ylmethyl)-amino]phenyl}sulfonyl}-2-(1H-pyrrolo[2,3-b]pyridin-5-yloxy)-benzamide shown in formula (I) is a Bcl-2 inhibitor, and Bcl-2 is the first member of the regulatory protein Bcl-2 family, It regulates cell death (apoptosis) by inducing (pro apoptotic) or inhibiting (anti apoptotic) apoptosis.

(I)

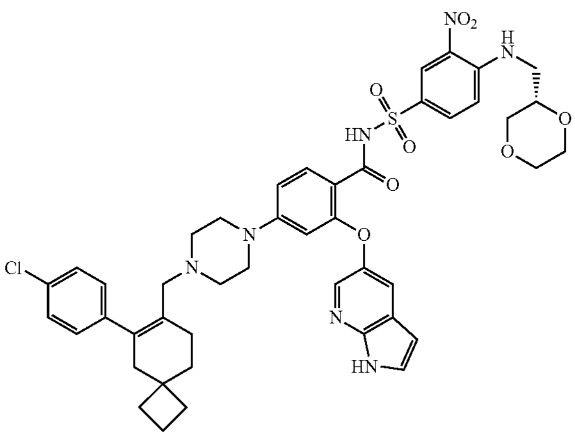

The compound is usually in crystalline form with very low solubility and is difficult to dissolve in aqueous media and most organic solvents such as methanol, ethanol, isopropanol, and acetone. To improve the solubility and dissolution of drugs in gastrointestinal solution and improve oral bioavailability, it is urgent to develop a preparation containing the compound with good stability and high dissolution.

SUMMARY OF THE INVENTION

The technical problem to be solved by the present invention is to overcome the defects of low solubility and difficult preparation of the existing Bcl-2 inhibitor, and provides a solid dispersion, preparation, preparation method, and application thereof. The solid dispersion has good dissolution and the solubility of effective constituents is significantly improved. The preparation can effectively improve the bioavailability of Bcl-2 inhibitor, has good dissolution and stability, and can improve drug safety.

To achieve the above object of the invention, the invention provides the following technical scheme:

The invention provides a solid dispersion comprising a carrier and an active ingredient, which is a compound as shown in formula (1) and/or a pharmaceutically acceptable salt thereof; The carrier is "homopolymer and copolymer of N-vinyl lactam" and/or pH-dependent cellulose derivatives.

(I)

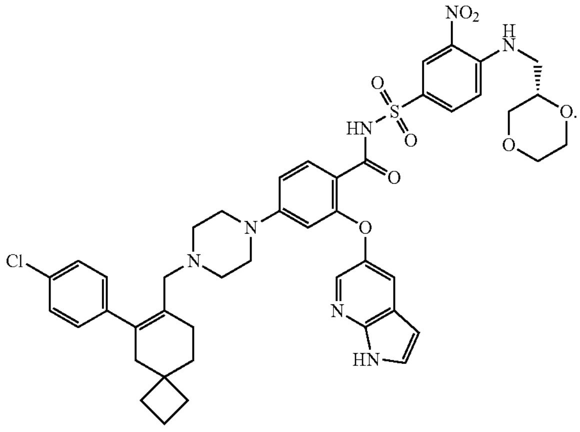

The compound of formula (I) is usually in crystalline form and has very low solubility. In an aqueous medium, 37° C. for 24 hours, in an acidic or neutral medium with a pH value of 1-7, the solubility is 0.0006-0.0003 mg/ml. Through research, the applicant unexpectedly found that by combining the compound of formula (1) with a suitable carrier, the compound of formula (I) can be highly dispersed in the carrier in an amorphous state. Based on maintaining a high drug loading, the solubility of the compound of formula (I) is greatly improved, and its dissolution rate and bioavailability are improved. The stability of solid dispersion is greatly improved. Even after high humidity (60%) and long-term (12 months) storage, the compound of formula (1) in the solid dispersion of the invention will not be transformed or degraded.

Preferably, the "homopolymer and the copolymer of N-vinyl lactam" are homopolymer (i.e. povidone or PVP) and copolymer of N-vinyl pyrrolidone; More preferably, it is povidone with a K value (viscosity of an aqueous solution of povidone) of about 12, about 25, about 30 or about 90 (for example, PVP-K12, PVP-K20, PVP-K30 or PVP-K90), or a copolymer of povidone (PVP) and polyvinyl acetate (PVP-VA series, for example, copolymer of 1-vinyl-2-pyrrolidone and vinyl acetate in a ratio of 6:4 by mass (PVP VA64), i.e. a copolymer formed by polymerization of polyvinyl pyrrolidone and polyvinyl acetate at 60:40).

Preferably, the povidone includes but is not limited to PVP K30.

Preferably, the copolymer of PVP and polyvinyl acetate includes but is not limited to PVP VA64.

Preferably, the pH-dependent cellulose derivative is hypromellose acetate succinate (HPMCAS); More preferably, the degree of substitution of acetyl group in the hypromellose acetate succinate can be 5%~9%, 7%~11% or 10~14%, and the degree of substitution of succinyl group can be 14~18%, 10~14% or 4~8% respectively.

Preferably, the hypromellose acetate succinate includes but is not limited to one or more of HPMCAS 716G, HPMCAS 912G, HPMCAS 126G, HPMCAS 716F, HPMCAS912F, HPMCAS126F, HPMCAS LG, HPMCAS MG, HPMCAS HG, HPMCAS LF, HPMCAS MF and HPMCAS HF, such as one or more of HPMCAS 716G, HPMCAS LG, HPMCAS 126G, HPMC AS HG, HPMCAS 912G and HPMCAS MG.

Preferably, the carrier is one or more of povidone, copovidone and hypromellose acetate succinate (HPMCAS); More preferably, the carrier is one or more of PVP K30, PVP VA64, HPMCAS 716G, HPMCAS LG, HPMCAS 126G, HPMC AS HG, HPMCAS 912G and HPMCAS MG, preferably one or more of PVP VA64, HPMCAS 716G and HPMCAS LG.

The dosage of the carrier can be conventional in the art. The mass ratio of the active ingredient to the carrier is preferably 1:(1~10), further preferably 1:(1.5~7) (for example, 1:1.5, 1:2, 3:7, 1:3, 1:4 or 1:6.7), and most preferably 1:(3~4). When the mass ratio of the active ingredient to the carrier is in the range of 1:(1.5~7), the solid dispersion has good effects in at least one aspect, such as equilibrium solubility, formability and dissolution. For example, the dissolution is better than that of the single active ingredient. When the mass ratio of the active ingredient to the carrier is in the range of 1:(3~4), the solid dispersion has better effects in at least one aspect, such as equilibrium solubility, formability and dissolution. For example, the dissolution can reach more than 90% at 60 min; When the temperature is 25° C. and the humidity is 60% RH, it remains amorphous and free of crystallization after 12 months of storage; Compared with the single active ingredient, the equilibrium solubility was significantly improved.

Preferably, the solid dispersion further comprises a surfactant.

When the solid dispersion also contains a surfactant, the type of surfactant can be conventional in the art. Preferably, the surfactant is one or more of Labrasol®, TPGS, Poloxamer and Tween80.

When the solid dispersion also contains a surfactant, the amount of the surfactant can be conventional in the art, and the mass ratio of the surfactant to the active ingredient is preferably (0.1~5): 1 (for example, 0.21:1, 0.33:1, 0.4:1, 0.58:1, 0.8:1 or 1.2:1), more preferably (0.1~2): 1.

Preferably, the solid dispersion further comprises a glidant.

When the solid dispersion also contains a glidant, the type of the glidant can be conventional in the art. Preferably, the glidant is colloidal silica.

When the solid dispersion also contains a glidant, the amount of the glidant can be conventional in the art, and the mass ratio of the glidant to the active ingredient is preferably (0.02~1): 1 (for example, 0.03:1, 0.04:1, 0.05:1, 0.06:1, 0.08:1 or 0.2:1), more preferably (0.02~0.2): 1.

In an example of the invention, the solid dispersion is an amorphous solid dispersion.

As a preferred scheme of the invention, the solid dispersion comprises the following constituents by mass: 1 part of the active ingredient and 1~10 parts of the carrier.

As a preferred scheme of the invention, the solid dispersion comprises the following constituents by mass: 1 part of the active ingredient and 1.5~7 parts of the carrier.

As a preferred scheme of the invention, the solid dispersion comprises the following constituents by mass: 1 part of the active constituent and 3~4 parts of the carrier.

As a preferred scheme of the invention, the solid dispersion comprises the following constituents by mass: 1 part of the active ingredient, 1~10 parts of the carrier and 0.1~5 parts of surfactant.

As a preferred scheme of the invention, the solid dispersion comprises the following constituents by mass: 1 part of the active ingredient, 1.5~7 parts of the carrier and 0.1~2 parts of surfactant.

As a preferred scheme of the invention, the solid dispersion comprises the following constituents by mass: 1 part of the active ingredient, 1~10 parts of the carrier and 0.02~1 part of the glidant.

As a preferred scheme of the invention, the solid dispersion comprises the following constituents by mass: 1 part of the active ingredient, 1.5-7 parts of the carrier and 0.02-0.2 parts of the glidant.

As a preferred scheme of the invention, the solid dispersion comprises the following constituents by mass: 1 part of the active ingredient, 1.5~7 parts of the carrier, 0.1~5 parts of surfactant and 0.02~0.2 parts of glidant.

As a preferred scheme of the invention, the solid dispersion comprises the following constituents by mass: 1 part of the active ingredient, 1.5~7 parts of the carrier, 0.1~2 parts of surfactant and 0.02~0.2 parts of glidant.

As a preferred scheme of the invention, the solid dispersion comprises the following constituents by mass: 1 part of the active ingredient and 4 parts of PVP VA 64.

As a preferred scheme of the invention, the solid dispersion comprises the following constituents by mass: 1 part of the active ingredient and 3 parts of PVP VA 64.

As a preferred scheme of the invention, the solid dispersion comprises the following constituents by mass: 1 part of the active ingredient and 4 parts of PVP K30.

As a preferred scheme of the invention, the solid dispersion comprises the following constituents by mass: 1 part of the active ingredient, 6.7 parts of PVP VA 64, 0.58 parts of Tween 80 and 0.0834 parts of colloidal silica.

As a preferred scheme of the invention, the solid dispersion comprises the following constituents by mass: I part of the active ingredient, 3 parts of HPMCAS 716 G and 0.08 parts of colloidal silica.

As a preferred scheme of the invention, the solid dispersion comprises the following constituents by mass: 1 part of the active ingredient, 3 parts of HPMCAS 126G and 0.08 parts of colloidal silica.

As a preferred scheme of the invention, the solid dispersion comprises the following constituents by mass: 1 part of the active ingredient, 3 parts of HPMCAS 912 G and 0.08 parts of colloidal silica.

As a preferred scheme of the invention, the solid dispersion comprises the following constituents by mass: 1 part of the active ingredient, 6.7 parts of HPMCAS 716 G and 0.08 parts of colloidal silica.

As a preferred scheme of the invention, the solid dispersion comprises the following constituents by mass: 1 part of the active ingredient, 3 parts of HPMCAS 716 G, 0.21 parts of Tween 80 and 0.08 parts of colloidal silica.

As a preferred scheme of the invention, the solid dispersion comprises the following constituents by mass: 1 part of the active ingredient, 3 parts of PVP VA64 and 1.2 parts of poloxamer.

As a preferred scheme of the invention, the solid dispersion comprises the following constituents by mass: 1 part of the active ingredient, 3 parts of PVP VA64 and 0.8 parts of TPGS.

As a preferred scheme of the invention, the solid dispersion comprises the following constituents by mass: 1 part of the active ingredient, 3 parts of PVP VA64 and 0.4 parts of Labrasol®.

As a preferred scheme of the invention, the solid dispersion comprises the following constituents by mass: 1 part of the active ingredient, 2 parts of HPMCAS 716G and 0.33 parts of TPGS.

The invention also provides a preparation method of the solid dispersion, including the following method 1, method 2 or method 3:

The method 1 comprises the following steps: mixing one or more of the compounds shown in formula I, its pharmaceutically acceptable salt, its crystal form and its solvate, and other constituents with a solvent to form a solution or suspension; Removing the solvent to obtain the solid dispersion;

The method 2 comprises the following steps: mixing one or more of the compounds shown in formula I, its pharmaceutically acceptable salt, its crystal form and its solvate, and other constituents, heating and extruding to obtain the solid dispersion;

The method 3 comprises the following steps: mixing the compounds shown in the formula I, the pharmaceutically acceptable salts, their crystalline forms and one or more of their solvent compounds, and other constituents, and mixing with the solvent, spray drying to obtain the solid dispersion.

In method 1, the type of solvent can be conventional in the art. Preferably, the solvent is one or more of water, alcohol solvent, ester solvent, ketone solvent, halohydrocarbon solvent, nitrile solvent and ether solvent. Wherein the alcohol solvent can be ethanol and/or methanol; The ester solvent can be ethyl acetate; The ketone solvent can be acetone; The halogenated hydrocarbon solvent can be dichloromethane; The nitrile solvent can be acetonitrile; The ether solvent can be tetrahydrofuran. Preferably, the solvent is acetone and/or ethanol.

In method 1, the amount of the solvent can be conventional in the art. Preferably, the mass volume ratio of "one or more of the compounds shown in formula I, its pharmaceutically acceptable salt, its crystal form and its solvate" to the solvent is (0.1~30): 1 mg/ml, and can be (1~10): 1 mg/ml.

In method 2, the extrusion temperature can be conventional in the art. Preferably, the extrusion temperature is 150~250° C., more preferably, the extrusion temperature is 160~220° C.

In method 2, preferably, the extrusion operation also includes a crushing step.

In method 3, the type of the solvent can be conventional in the art. Preferably, the solvent is an alcohol solvent and/or a halogenated hydrocarbon solvent, wherein the alcohol solvent can be methanol; The halogenated hydrocarbon solvent can be dichloromethane. Preferably, the solvent is ethanol and dichloromethane, wherein the volume ratio of ethanol and dichloromethane is preferably 5:95.

In method 3, the amount of solvent can be conventional in the art. Preferably, the mass volume ratio of "one or more of the compounds shown in formula I, its pharmaceutically acceptable salt, its crystal form and its solvate" to the solvent is (0.1~30): 1 mg/ml.

In method 3, preferably, the spray drying material temperature can be set at 40° C.~200° C., preferably 50° C.~110° C.

The invention also provides a preparation comprising the solid dispersion, which comprises the solid dispersion, the filler and the disintegrating agent.

In the preparation, the type of filler can be conventional in the art. Preferably, the filler is one or more of microcrystalline cellulose, lactose, pregelatinized starch, calcium hydrogen phosphate and calcium phosphate; For example, microcrystalline cellulose, lactose, calcium hydrogen phosphate, a combination of microcrystalline cellulose and lactose, a combination of microcrystalline cellulose and pregelatinized starch, or "a combination of microcrystalline cellulose and calcium phosphate"; More preferably, the filler is calcium hydrogen phosphate or "a combination of microcrystalline cellulose and calcium phosphate".

When the filler is a combination of microcrystalline cellulose and calcium phosphate, preferably, the mass ratio of microcrystalline cellulose and calcium phosphate is 1:(0.5~2) (for example, 1:0.5, 1:1 or 1:2), more preferably 1:(1~2), preferably 1:1.

Wherein, when the filler contains microcrystalline cellulose, the type of microcrystalline cellulose can be conventional in the art. Preferably, the microcrystalline cellulose is one or more of microcrystalline cellulose Avicel® PH102, silicified microcrystalline cellulose 90, silicified microcrystalline cellulose HD90, microcrystalline cellulose PH105, microcrystalline cellulose KG802 and microcrystalline cellulose Avicel® PH101, more preferably, the microcrystalline cellulose is microcrystalline cellulose Avicel® PH102 and/or microcrystalline cellulose KG802.

In the preparation, the dosage of the filler can be conventional in the art. Preferably, based on the mass of the solid dispersion of 1 part, the number of mass parts of the filler is 0.2~8 parts; More preferably, the number of mass parts of the filler is 0.2~2 parts, such as 0.25 parts, 0.40 parts, 0.43 parts, 0.72 parts, 0.84 parts, 0.85 parts, 0.86 parts or 0.90 parts.

In the preparation, the type of the disintegrating agent can be conventional in the art. Preferably, the disintegrating agent is one or more of croscarmellose sodium, Low-substituted hydroxypropyl cellulose and carboxymethyl starch sodium; More preferably, the disintegrating agent is croscarmellose sodium.

In the preparation, the dosage of the disintegrating agent can be conventional in the art. Preferably, when the mass of the solid dispersion is 1 part, the mass part of the disintegrating agent is 0.03~0.4 parts; More preferably, the mass fraction of the disintegrating agent is 0.05~0.3, such as 0.075, 0.09, 0.1 and 0.14.

The preparation preferably further comprises glidants.

When the preparation also comprises glidants, the type of the glidants can be conventional in the art. Preferably, the glidants is colloidal silica.

When the preparation also comprises glidants, the dosage of the glidants can be conventional in the art. Preferably, the mass fraction of the glidants is 0.006~0.2 parts based on the mass of the solid dispersion; More preferably, the mass fraction of the glidants is 0.01~0.06; For example, 0.01, 0.02, 0.03 or 0.04.

Preferably, the preparation further comprises a lubricant.

When the preparation also contains a lubricant, the type of lubricant can be conventional in the art. Preferably, the lubricant is magnesium stearate and/or Sodium stearyl fumarate.

When the preparation also contains a lubricant, the amount of the lubricant can be conventional in the art. Preferably, the number of parts by mass of the lubricant is 0.004~0.1 parts based on the mass of the solid dispersion is 1 part; More preferably, the mass fraction of the lubricant is 0.004~0.04; For example, 0.006, 0.007, 0.01 or 0.02.

Preferably, the preparation further comprises a coating material.

When the preparation also comprises a coating material, the type of the coating materials can be conventional in the art. Preferably, the coating material is a gastric soluble film coating premix, such as Opaday® II.

When the preparation also comprises a coating material, the dosage of the coating materials can be conventional in the art. Preferably, the number of parts by mass of the coating materials is 0.01~0.2 parts based on the mass of the solid dispersion is 1 part; More preferably, the number of parts by mass of the coating materials is 0.04~0.1 parts, such as 0.06 parts.

As a preferred scheme of the invention, the preparation comprises the following constituents by mass: 1 part of the solid dispersion, 0.2~8 parts of the filler and 0.03~0.4 parts of the disintegrating agent.

As a preferred scheme of the invention, the preparation comprises the following constituents by mass: 1 part of the solid dispersion, 0.2~2 parts of the filler and 0.05~0.3 parts of the disintegrating agent.

As a preferred scheme of the invention, the preparation comprises the following constituents by weight: 1 part of the solid dispersion, 0.2~8 parts of the filler, 0.03~0.4 parts of the disintegrating agent and 0.006~0.2 parts of the glidant.

As a preferred scheme of the invention, the preparation comprises the following constituents by mass: 1 part of the solid dispersion, 0.2~2 parts of the filler, 0.05~0.3 parts of the disintegrating agent and 0.01~0.06 parts of the glidant.

As a preferred scheme of the invention, the preparation comprises the following constituents by weight: 1 part of the solid dispersion, 0.2~8 parts of the filler, 0.03~0.4 parts of the disintegrating agent, 0.006~0.2 parts of glidant and 0.004~0.1 parts of lubricant.

As a preferred scheme of the invention, the preparation comprises the following constituents by mass: 1 part of the solid dispersion, 0.2~2 parts of the filler, 0.05~0.3 parts of the disintegrating agent, 0.01~0.06 parts of glidant and 0.004~0.04 parts of lubricant.

As a preferred scheme of the invention, the preparation comprises the following constituents by weight: 1 part of the solid dispersion, 0.2~8 parts of the filler, 0.03~0.4 parts of the disintegrating agent, 0.006~0.2 parts of the glidant, 0.004~0.1 parts of the lubricant and 0.01~0.2 parts of the coating material.

As a preferred scheme of the invention, the preparation comprises the following constituents by mass: 1 part of the solid dispersion, 0.2~2 parts of the filler, 0.05~0.3 parts of the disintegrating agent, 0.01~0.06 parts of the glidant, 0.004~0.04 parts of the lubricant and 0.04~0.1 parts of the coating material.

As a preferred scheme of the invention, the preparation comprises the following constituents by mass: 1 part of the solid dispersion and 0.05 part of colloidal silica.

As a preferred scheme of the invention, the preparation comprises the following constituents by mass: 1 part of the solid dispersion and 0.9 part of microcrystalline cellulose (Avicel® PH102) and 0.1 part of croscarmellose sodium.

As a preferred scheme of the invention, the preparation comprises the following constituents by mass: 1 part of the solid dispersion and 0.6 part of microcrystalline cellulose (Avicel® PH102), 0.3 parts lactose and 0.1 parts croscarmellose sodium.

As a preferred scheme of the invention, the preparation comprises the following constituents by mass: 1 part of the solid dispersion and 0.6 part of microcrystalline cellulose (Avicel® PH102), 0.3 parts of pregelatinized starch and 0.1 parts of croscarmellose sodium.

As a preferred scheme of the invention, the preparation comprises the following constituents by mass: 1 part of the solid dispersion and 0.6 part of microcrystalline cellulose (Avicel® PH102), 0.3 parts of calcium phosphate and 0.1 parts of croscarmellose sodium.

As a preferred scheme of the invention, the preparation comprises the following constituents by mass: 1 part of the solid dispersion and 0.45 part of microcrystalline cellulose (Avicel® PH102), 0.45 parts of calcium phosphate and 0.1 parts of croscarmellose sodium.

As a preferred scheme of the invention, the preparation comprises the following constituents by mass: 1 part of the solid dispersion and 0.3 part of microcrystalline cellulose (Avicel® PH102), 0.6 parts of calcium phosphate and 0.1 parts of croscarmellose sodium.

As a preferred scheme of the invention, the preparation comprises the following constituents by mass: 1 part of the solid dispersion and 0.428 parts of microcrystalline cellulose (Avicel® PH102), 0.428 parts of calcium phosphate, 0.1 parts of croscarmellose sodium, 0.04 parts of colloidal silica and 0.06 parts of magnesium stearate.

As a preferred scheme of the invention, the preparation comprises the following constituents by mass: 1 part of the solid dispersion, 0.45 part of silicified microcrystalline cellulose 90, 0.45 part of calcium phosphate and 0.1 part of croscarmellose sodium.

As a preferred scheme of the invention, the preparation comprises the following constituents by mass: 1 part of the solid dispersion, 0.45 part of silicified microcrystalline cellulose HD 90, 0.45 part of calcium phosphate and 0.1 part of croscarmellose sodium.

As a preferred scheme of the invention, the preparation comprises the following constituents by mass: 1 part of the solid dispersion, 0.43 part of microcrystalline cellulose PH105, 0.43 part of calcium phosphate, 0.1 part of croscarmellose sodium and 0.04 part of colloidal silica.

As a preferred scheme of the invention, the preparation comprises the following constituents by mass: 1 part of the solid dispersion, 0.43 part of microcrystalline cellulose KG802, 0.43 part of calcium phosphate, 0.1 part of croscarmellose sodium and 0.04 part of colloidal silica.

As a preferred scheme of the invention, the preparation comprises the following constituents by mass: 1 part of the solid dispersion and 0.42 part of microcrystalline cellulose (Avicel® PH101) and 0.07 parts of croscarmellose sodium.

As a preferred scheme of the invention, the preparation comprises the following constituents by mass: 1 part of the solid dispersion and 0.42 part of microcrystalline cellulose (Avicel® PH101) and 0.07 parts of low-substituted hydroxypropyl cellulose.

As a preferred scheme of the invention, the preparation comprises the following constituents by mass: 1 part of the solid dispersion and 0.39 part of microcrystalline cellulose (Avicel® PH101), 0.07 parts of croscarmellose sodium and 0.03 parts of colloidal silica.

As a preferred scheme of the invention, the preparation comprises the following constituents by mass: 1 part of the solid dispersion and 0.3 part of microcrystalline cellulose (Avicel® PH101), 0.6 parts of calcium phosphate, 0.1 parts of croscarmellose sodium and 0.06 parts of colloidal silica.

As a preferred scheme of the invention, the preparation comprises the following constituents by mass: 1 part of the solid dispersion and 0.3 part of microcrystalline cellulose (Avicel® PH101), 0.6 parts of calcium phosphate, 0.1 parts of croscarmellose sodium, 0.04 parts of colloidal silica and 0.01 parts of magnesium stearate.

As a preferred scheme of the invention, the preparation comprises the following constituents by mass: 1 part of the solid dispersion, 0.42 part of microcrystalline cellulose KG802, 0.42 part of calcium phosphate, 0.1 part of croscarmellose sodium, 0.04 part of colloidal silica and 0.02 part of magnesium stearate.

As a preferred scheme of the invention, the preparation comprises the following constituents by mass: 1 part of the solid dispersion and 0.43 part of microcrystalline cellulose (Avicel® PH102), 0.43 parts of calcium phosphate, 0.1 parts of croscarmellose sodium, 0.04 parts of colloidal silica, 0.02 parts of magnesium stearate and 0.006 parts of gastric soluble film coating premix (Opadry® II).

As a preferred scheme of the invention, the preparation comprises the following constituents by mass: 1 part of the solid dispersion, 0.42 part of microcrystalline cellulose KG802, 0.42 part of calcium phosphate, 0.1 part of croscarmellose sodium, 0.04 part of colloidal silica, 0.02 part of magnesium stearate and 0.06 part of gastric soluble film coating premix (Opadry® II).

As a preferred scheme of the invention, the preparation comprises the following constituents by mass: 1 part of the solid dispersion, 0.26 part of calcium hydrogen phosphate, 0.01 part of colloidal silica and 0.006 part of sodium stearyl fumarate.

As a preferred scheme of the invention, the preparation comprises the following constituents by mass: 1 part of the solid dispersion, 0.26 part of calcium hydrogen phosphate, 0.1 part of croscarmellose sodium, 0.01 part of colloidal silica and 0.007 part of sodium stearyl fumarate.

As a preferred scheme of the invention, the preparation comprises the following constituents by mass: 1 part of the solid dispersion, 0.36 part of microcrystalline cellulose, 0.36 part of calcium phosphate, 0.1 part of croscarmellose sodium, 0.04 part of colloidal silica and 0.02 part of magnesium stearate.

The invention also provides a preparation method of the preparation containing the solid dispersion, which comprises the following steps: mixing the constituents of the preparation.

In the preparation method of the preparation, preferably, each constituent is crushed first and then mixed.

The invention also provides the application of the preparation containing the solid dispersion in the preparation of drugs for the treatment of hyperproliferative diseases.

Preferably, the hyperproliferative disease is cancer.

Preferably, the cancer is selected from acute monocytic leukemia, acute myelogenous leukemia, chronic myelogenous leukemia, chronic lymphocytic leukemia, mixed lineage leukemia, NUT-midline cancer, multiple myeloma, small cell lung cancer, neuroblastoma, lymphoma, cervical cancer, esophageal cancer, ovarian cancer, colorectal cancer, prostate cancer and breast cancer.

Based on not violating the common knowledge in the art, the above-preferred conditions can be combined at will to obtain the better examples of the invention.

The reagents and raw materials used in the invention are commercially available.

The positive progressive effect of the invention is that the solid dispersion provided by the invention can highly disperse the active ingredients in the carrier in an amorphous state, improve the dissolution of the compound of formula (I) in gastrointestinal fluid, improve its dissolution rate and bioavailability, and greatly improve the stability of the solid dispersion based on maintaining a high drug loading. The preparation of the invention has good dissolution, low impurity content (total impurity content is less than 2%, the maximum single impurity content is less than 0.5%), small-batch difference and good content uniformity.

SPECIFIC EMBODIMENTS

Figure 1:
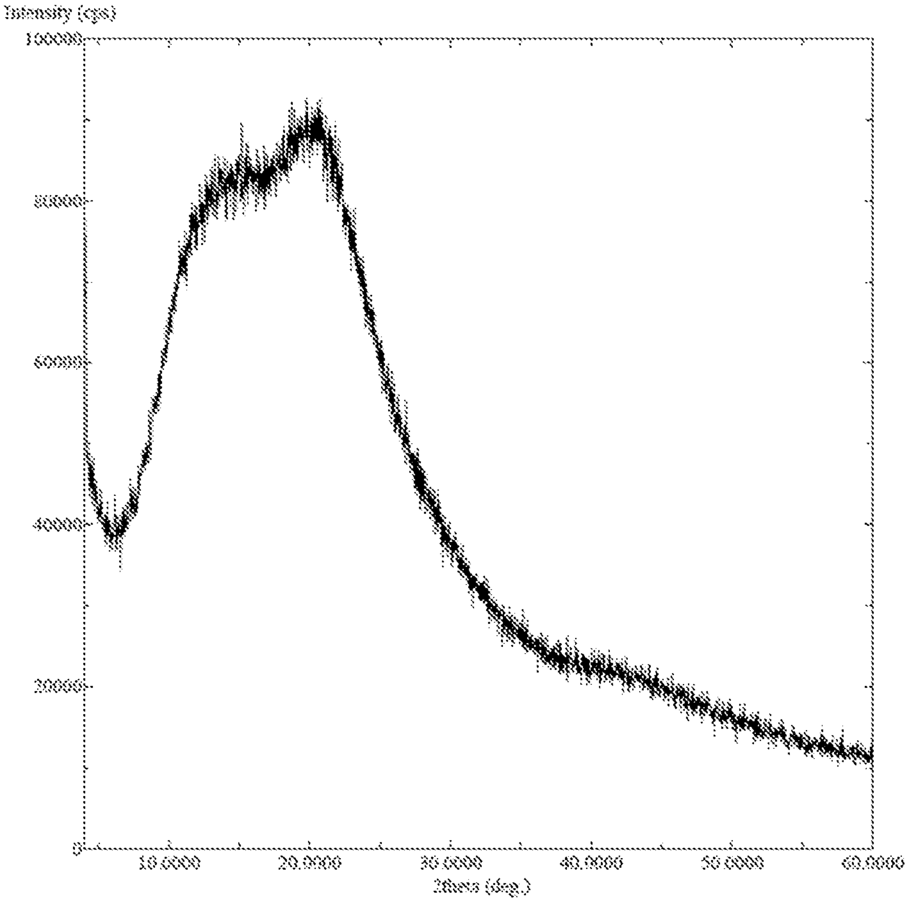
FIG. 1 shows the XRD pattern of the solid dispersion of example 7.

The invention will be further described by way of examples, but the invention is not limited to the scope of the examples. The experimental methods without specific conditions in the following examples shall be selected according to the conventional methods and conditions or according to the commodity instructions.

In the following examples, the reagents and raw materials used are commercially available.

X-ray powder diffraction determination conditions: Cu 40 kV/40 mA, step size of 0.02°, scanning speed of 60°/min, range of 4°~60°.

DSC test conditions: place the test sample in a closed aluminum plate and raise the temperature to about 240° C. at the rate of 10° C./min under nitrogen flow to obtain the differential scanning calorimetry (DSC) curve.

In the following examples, the compound of formula (I) is prepared according to WO2018/027097A1, then the compound of formula (I) is placed in a bottle, an appropriate amount of conventional solvents such as acetone, acetonitrile, ethyl acetate, 1,4-dioxane, toluene or ethanol are added, standing at room temperature, the obtained crystal form is centrifuged and dried at room temperature to obtain the crystalline form of compound (1).

Example 1: Preparation Method of Compound of Formula (I)

Prepare the compound of formula (I) according to WO2018/027097A1, put the compound of formula (I) in a bottle, add an appropriate amount of 1,4-dioxane, stand at room temperature for 2 days, centrifuge the obtained crystal form, and dry at room temperature to obtain the crystalline form of compound (I).

Example 2: Preparation Method of Compound of Formula (I)

Prepare the compound of formula (1) according to WO2018/027097A1, put the compound of formula (I) in a bottle, add an appropriate amount of ethanol, stir at room temperature for 5 days, centrifuge, add acetone to the obtained crystal form, stir at room temperature for 1.5 hours, centrifuge, and dry at room temperature to obtain the crystalline form of acetone solvate.

Example 3: Preparation Method of Compound of Formula (I)

Prepare the compound of formula (I) according to WO2018/027097A1, put the compound of formula (I) in a bottle, add an appropriate amount of acetonitrile solvent, stir at room temperature for 5 days, centrifuge the obtained crystal form and dry at room temperature to obtain the crystalline form of acetonitrile solvate.

Amorphous or other crystalline forms of compounds of formula (I) can also be used to prepare solid dispersions. Of course, the solid dispersion can also be prepared using the salt of the compound of formula (I).

Example 4: Preparation Method of Solid Dispersion

The solid dispersion is prepared by the following vacuum evaporation method: accurately weigh about 100 mg of the crystalline form (hereinafter referred to as "API") of compound (I) prepared in example 1, place it in a 100 ml round bottom flask, add 20 ml of acetone and shake to dissolve it; Accurately weigh a certain amount of carrier, place it in the same round bottom flask, add an appropriate amount of acetone or ethanol to completely dissolve it, mix it evenly by ultrasound, place it on the rotary evaporator, heat and rotate at 60° C., gradually add vacuum, when boiling occurs in the round bottom flask, increase the temperature to 80° C. until the solvent is volatilized, and take it out after continuous rotary evaporation for 1 h to obtain solid dispersion powder.

In this example, the mass ratio of the crystalline form of compound (I) to PVP VA64 is 1:4, that is, the drug loading is 20%.

Drug dissolution test was performed on the solid dispersion (rotating basket method, 0.2% SDS solution, 500 ml, 100 rpm). The results showed that the drug dissolution rates of 10 min, 30 min and 60 min were 67.47%, 88.99% and 95.86%, respectively. Under the same conditions, the drug dissolution of API (compound prepared in example 1) in 10 min, 30 min and 60 min were 7%, 13% and 22% respectively.

Example 5: Preparation Method of Solid Dispersion

The PVP VA64 in example 4 was replaced by PVP K30, and the solid dispersion was prepared and characterized by the same method as in example 4. The drug dissolution of solid dispersion was tested by the rotating basket method (0.2% SDS solution, 500 ml and 100 rpm). The results showed that the drug dissolution of 10 min, 30 min and 60 min were 36.59%, 71.47% and 84.39% respectively.

Example 6: Preparation Method of Solid Dispersion

The crystalline form of compound (I) in example 4 and the mass ratio of PVP VA64 were replaced with 1:3, that is, the drug loading was replaced with 25%. The solid dispersion was prepared and characterized by the same method as in example 4. The drug dissolution of solid dispersion was tested by the rotating basket method (0.2% SDS solution, 500 ml and 100 rpm). The results showed that the drug dissolution of 10 min, 30 min and 60 min were 68.46%, 89.56% and 92.73% respectively.

Example 7: Preparation Method of Solid Dispersion

Weigh the API prepared in example 1, carrier PVP VA64 and colloidal silica (wherein the mass proportions of API, carrier PVP VA64 and colloidal silica are 23.75%, 71.25% and 5.00% respectively) through 30 mesh sieves, mix the API and PVP VA64 in the mixing barrel at 20 rpm for 10 minutes, and then add them into the hot-melt extrusion hopper for hot-melt extrusion. Process parameters: 195° C. Feed speed: 50 g/min, screw speed: 135 rpm, the prepared extrudate is crushed, the prescribed amount of glidant colloidal silica is added, and the solid dispersion is prepared by mixing in the mixing barrel at 20 rpm for 10 minutes.

Figure 2:
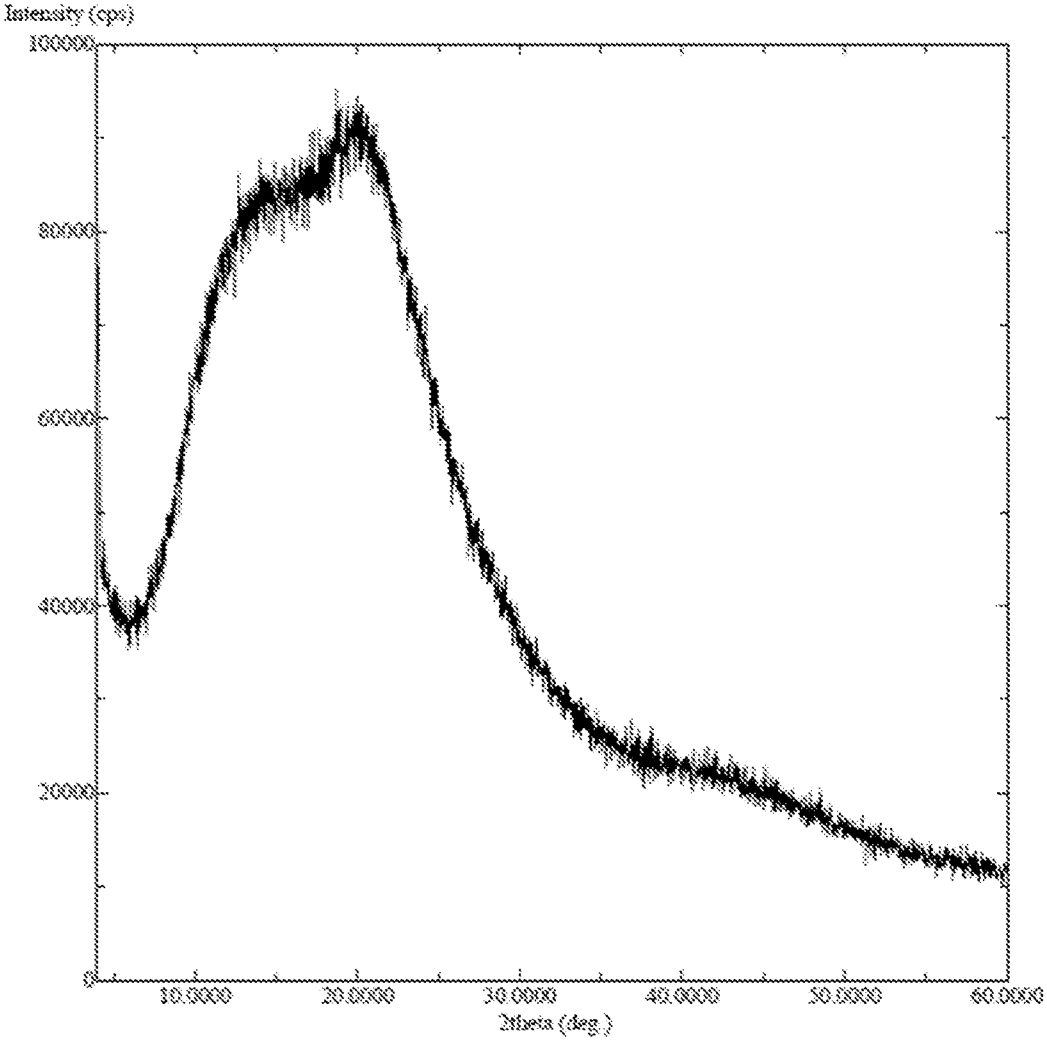
FIG. 2 shows the XRD pattern of solid dispersion in example 7 after long-term placement.

The prepared solid dispersion was characterized by XRD scanning. See FIG. 1. The active ingredients were dispersed in the carrier in an amorphous state. In order to investigate the stability of the solid dispersion, the solid dispersion was placed for 12 months at a temperature of 25° C. and a humidity of 60% RH, and the solid dispersion was scanned by XRD again. The results are shown in FIG. 2. The results show that the solid dispersion still maintains an amorphous state without any crystallization.

Example 8: Preparation Method of Pharmaceutical Preparations

The API prepared in example 1 and carrier PVP VA64 are respectively sieved through 30 mesh screens, added into the hopper mixer according to the proportion of drug load of 25% (i.e. drug load ratio of 1:3), mixed at the mixing speed of 20 rpm for 10 minutes, and hot-melt extrusion is carried out in the hot-melt extruder. The process parameters are: operation temperature 195° C., feed speed: about 50 rpm, screw speed: 135 rpm; The extrudate obtained is a solid dispersion.

Weigh the solid dispersion and microcrystalline cellulose (Avicel® PH102) and croscarmellose sodium (wherein including solid dispersion, microcrystalline cellulose (Avicel® PH102) and croscarmellose sodium account for 50%, 45% and 5% of the total material respectively). The solid dispersion, microcrystalline cellulose (Avicel® PH102) and croscarmellose sodium are crushed, passed through 30 mesh screens, mixed in hopper mixer, rotating speed of 20 rpm and mixing time of 10 minutes.

The tablets were pressed on the experimental tablet press (ZP14) with a 10 mm Round die to make a plain tablet with a tablet weight of 400 mg. The parameters of plain tablets were tested, in which the average hardness was 100N, the average thickness was 5.87 mm, and the disintegration time was 5 minutes and 30 seconds.

Example 9: Preparation Method of Preparation

Weigh the solid dispersion, microcrystalline cellulose (Avicel® PH102), lactose and croscarmellose sodium prepared in example 8 (wherein the mass proportions of solid dispersion, microcrystalline cellulose (Avicel® PH102), lactose and croscarmellose sodium in the total material are 50%, 30%, 15% and 5% respectively), and sieve, crush and mix the solid dispersion, microcrystalline cellulose (Avicel® PH102), lactose and croscarmellose sodium, The specific operation and parameters are the same as those in example 8.

The tablets were pressed on the experimental tablet press (ZP14) with a 10 mm Round die to make a plain tablet with a tablet weight of 400 mg. The parameters of the plain tablets were tested, in which the average hardness was 51N, the average thickness was 5.81 mm, and the disintegration time was 3 minutes and 55 seconds.

Example 10: Preparation Method of Pharmaceutical Preparations

Weigh the solid dispersion prepared in example 8, microcrystalline cellulose (Avicel® PH102), pregelatinized starch and croscarmellose sodium (wherein the mass proportions of solid dispersion, microcrystalline cellulose (Avicel® PH102), pregelatinized starch and croscarmellose sodium in the total material are 50%, 30%, 15% and 5%, respectively) The solid dispersion, microcrystalline cellulose (Avicel® PH102), pregelatinized starch and croscarmellose sodium are screened, crushed and mixed. The specific operation and parameters are the same as those in example 8.

The tablets were pressed on the experimental tablet press (ZP14) with a 10 mm Round die to make a plain tablet with a tablet weight of 400 mg. The parameters of plain tablets were tested, in which the average hardness was 57N, the average thickness was 5.81 mm, and the disintegration time was 4 minutes and 16 seconds.

Example 11: Preparation Method of Pharmaceutical Preparations

Weigh the solid dispersion prepared in example 8, microcrystalline cellulose (Avicel® PH102), calcium phosphate and croscarmellose sodium (wherein the mass proportions of solid dispersion, microcrystalline cellulose (Avicel® PH102), calcium phosphate and croscarmellose sodium in the total material are 50%, 30%, 15% and 5% respectively), the solid dispersion, microcrystalline cellulose (Avicel® PH102), calcium phosphate and croscarmellose sodium are screened, crushed and mixed. The specific operation and parameters are the same as those in example 8.

The tablets were pressed on the experimental tablet press (ZP14) with a 10 mm Round die to make a plain tablet with a tablet weight of 400 mg. The parameters and drug dissolution of plain tablets were tested. The average hardness was 59N, the average thickness was 5.29 mm, and the disintegration time was 49 seconds.

Dissolution determination: adopt the method II of Pharmacopoeia dissolution determination (paddle method), take 900 ml pH 6.8 phosphate solution (0.2% sodium dodecyl sulfate) as the dissolution medium, the rotating speed is 75 revolutions per minute, and the cumulative dissolution after 45 minutes is not less than 75% of the marked amount. The drug dissolution of the preparation in 5 min, 15 min, 30 min, 45 min, 60 min, 90 min and 120 min is 14%, 39%, 63%, 76%, 83%, 90% and 91% respectively.

Example 12: Preparation Method of Pharmaceutical Preparations

Weigh the solid dispersion prepared in example 8, microcrystalline cellulose (Avicel® PH102), calcium phosphate and croscarmellose sodium (wherein the mass proportions of solid dispersion, microcrystalline cellulose (Avicel® PH102), calcium phosphate and croscarmellose sodium in the total material are 50%, 30%, 15% and 5% respectively), the solid dispersion, microcrystalline cellulose (Avicel® PH102), calcium phosphate and croscarmellose sodium are screened, crushed and mixed. The specific operation and parameters are the same as those in example 8.

The tablets were pressed on the experimental tablet press (ZP14) with a 10 mm Round die to make a plain tablet with a tablet weight of 400 mg. The parameters of plain tablets were tested, in which the average hardness was 78N, the average thickness was 5.05 mm, and the disintegration time was 3 minutes and 22 seconds.

Example 13: Preparation Method of Pharmaceutical Preparations

Weigh the solid dispersion prepared in example 8, microcrystalline cellulose (Avicel® PH102), calcium phosphate and croscarmellose sodium (wherein the mass proportions of solid dispersion, microcrystalline cellulose (Avicel® PH102), calcium phosphate and croscarmellose sodium in the total material are 50%, 22.5%, 22.5% and 5% respectively), the solid dispersion, microcrystalline cellulose (Avicel® PH102), calcium phosphate and croscarmellose sodium are screened, crushed and mixed. The specific operation and parameters are the same as those in example 8.

The tablets were pressed on the experimental tablet press (ZP14) with a 10 mm Round die to make a plain tablet with a tablet weight of 400 mg. The parameters of plain tablets were tested, in which the average hardness was 78N, the average thickness was 4.95 mm, and the disintegration time was 3 minutes and 7 seconds.

Example 14: Preparation Method of Pharmaceutical Preparations

Weigh the solid dispersion prepared in example 8, microcrystalline cellulose (Avicel® PH102), calcium phosphate and croscarmellose sodium (wherein the mass proportions of solid dispersion, microcrystalline cellulose (Avicel® PH102), calcium phosphate and croscarmellose sodium in the total material are 50%, 15%, 30% and 5% respectively), the solid dispersion, microcrystalline cellulose (Avicel® PH102), calcium phosphate and croscarmellose sodium are screened, crushed and mixed. The specific operation and parameters are the same as those in example 8.

The tablets were pressed on the experimental tablet press (ZP14) with a 10 mm Round die to make a plain tablet with a tablet weight of 400 mg. The parameters of plain tablets were tested, in which the average hardness was 79N, the average thickness was 4.84 mm, and the disintegration time was 2 minutes and 21 seconds.

Example 15: Preparation Method of Pharmaceutical Preparations

Weigh the solid dispersion prepared in example 8, microcrystalline cellulose (Avicel® PH102), calcium phosphate, croscarmellose sodium, colloidal silica and magnesium stearate (wherein the mass proportions of solid dispersion, microcrystalline cellulose (Avicel® PH102), calcium phosphate, croscarmellose sodium, colloidal silica and magnesium stearate in the total material are 50%, 21.4%, 21.4% and 5% respectively 2% and 0.3%), the solid dispersion, microcrystalline cellulose (Avicel® PH102), calcium phosphate, croscarmellose sodium, colloidal silica and magnesium stearate are sieved, crushed and mixed. The specific operation and parameters are the same as those in example 8.

The tablets were pressed on the experimental tablet press (ZP14) with a 10 mm Round die to make a plain tablet with a tablet weight of 400 mg. The parameters and drug dissolution of plain tablets were tested, in which the average hardness was 50N and the average thickness was 5.10 mm. In plain tablets, the content (calculated as dry product) is 100.2%, the total impurity is 1.76%, and the dissolution (paddle method, using 900 ml of pH6.8 phosphate solution (0.2% sodium dodecyl sulfate) as the dissolution medium, and the rotating speed is 75 rpm). The dissolution in 5 min, 30 min, 45 min, 60 min, 90 min and 120 min are 5%, 64%, 84%, 93%, 98% and 98% respectively.

Example 16: Preparation Method of Pharmaceutical Preparations

Weigh the solid dispersion prepared in example 8, silicified microcrystalline cellulose 90, calcium phosphate and croscarmellose sodium (wherein the mass proportions of solid dispersion, silicified microcrystalline cellulose 90, calcium phosphate and croscarmellose sodium in the total material are 50%, 22.5%, 22.5% and 5%, respectively), the solid dispersion, silicified microcrystalline cellulose 90, calcium phosphate and croscarmellose sodium were screened, crushed and mixed. The specific operation and parameters were the same as those in example 8.

The tablets were pressed on the experimental tablet press (ZP14) with a 10 mm Round die to make a plain tablet with a tablet weight of 400 mg. Test the parameters of the plain sheet, in which the average hardness is 65N and the average thickness is 5.11 mm.

Example 17: Preparation Method of Pharmaceutical Preparations

Weigh the solid dispersion prepared in example 8, silicified microcrystalline cellulose HD 90, calcium phosphate and croscarmellose sodium (wherein the mass proportions of solid dispersion, silicified microcrystalline cellulose HD 90, calcium phosphate and croscarmellose sodium in the total material are 50%, 22.5%, 22.5% and 5%, respectively), the solid dispersion, silicified microcrystalline cellulose HD 90, calcium phosphate and croscarmellose sodium are sieved, crushed and mixed. The specific operation and parameters are the same as those in example 8.

The tablets were pressed on the experimental tablet press (ZP14) with a 10 mm of the plain sheet, in which the average hardness is 43N and the average thickness is 5.09 mm.

Example 18: Preparation Method of Pharmaceutical Preparations

Weigh the solid dispersion prepared in example 8, microcrystalline cellulose PH105, calcium phosphate, croscarmellose sodium and colloidal silica (wherein the mass proportions of solid dispersion, microcrystalline cellulose PH105, calcium phosphate, croscarmellose sodium and colloidal silica in the total material are 50%, 21.5%, 21.5%, 5% and 2%, respectively), the solid dispersion, microcrystalline cellulose PH105, calcium phosphate, croscarmellose sodium and colloidal silica are screened, crushed and mixed. The specific operation and parameters are the same as those in example 8.

The tablets were pressed on the experimental tablet press (ZP14) with a 10 mm Round die to make a plain tablet with a tablet weight of 400 mg. Test the parameters of the plain sheet, in which the average hardness is 75N and the average thickness is 5.12 mm.

Example 19: Preparation Method of Pharmaceutical Preparations

Weigh the solid dispersion prepared in example 8, microcrystalline cellulose KG802, calcium phosphate, croscarmellose sodium and colloidal silica (wherein the mass proportions of solid dispersion, microcrystalline cellulose KG802, calcium phosphate, croscarmellose sodium and colloidal silica in the total material are 50%, 21.5%, 21.5%, 5% and 2%, respectively), the solid dispersion, microcrystalline cellulose KG802, calcium phosphate, croscarmellose sodium and colloidal silica are screened, crushed and mixed. The specific operation and parameters are the same as those in example 8.

The tablets were pressed on the experimental tablet press (ZP14) with a 10 mm of the plain sheet, in which the average hardness is 93N and the average thickness is 5.10 mm.

It can be seen from examples 15~19 that the type of microcrystalline cellulose has a certain impact on the hardness of the tablet, but has little impact. Among them, the tablet prescription containing microcrystalline cellulose KG802, has the greatest hardness and the best compression formability under the same level of tablet thickness.

Example 20: Preparation Method of Pharmaceutical Preparations

Weigh the solid dispersion, microcrystalline cellulose (Avicel® PH101) and croscarmellose sodium prepared in example 8 (wherein the mass proportions of solid dispersion, microcrystalline cellulose (Avicel® PH101) and croscarmellose sodium in the total material are 66.7%, 28.3% and 5% respectively), the solid dispersion, microcrystalline cellulose (Avicel® PH101) and croscarmellose sodium are screened, crushed and mixed. The specific operation and parameters are the same as those in example 8.

The tablets were pressed on the experimental tablet press (ZP14) with a 10 mm Round die to make plain tablets with a tablet weight of 300 mg. The parameters and drug dissolution of plain tablets were tested, in which the average hardness was 35N and the average thickness was 4.94 mm. In terms of dissolution (paddle method, taking 900 ml pH 6.8 phosphate solution (0.2% sodium dodecyl sulfate) as the dissolution medium and the rotating speed is 75 rpm), the drug dissolution in 5 min, 15 min, 30 min, 45 min, 60 min, 90 min and 120 min are 1%, 10%, 33%, 53%, 67%, 85% and 93% respectively.

Example 21: Preparation Method of Pharmaceutical Preparations

Weigh the solid dispersion prepared in example 8, microcrystalline cellulose (Avicel® PH101) and low-substituted hydroxypropyl cellulose sodium (wherein the mass proportions of solid dispersion, microcrystalline cellulose (Avicel® PH101) and low-substituted hydroxypropyl cellulose sodium in the total material are 66.7%, 28.3% and 5% respectively), the solid dispersion, microcrystalline cellulose (Avicel® PH101) and low-substituted hydroxypropyl cellulose sodium are screened, crushed and mixed. The specific operation and parameters are the same as those in example 8.

The tablets were pressed on the experimental tablet press (ZP14) with a 10 mm Round die to make plain tablets with a tablet weight of 300 mg. The parameters and drug dissolution of plain tablets was tested, in which the average hardness was 31N and the average thickness was 5.10 mm. In terms of dissolution (paddle method, taking 900 ml of pH 6.8 phosphate solution (0.2% sodium dodecyl sulfate) as the dissolution medium and the rotating speed is 75 rpm), the drug dissolution in 5 min, 15 min, 30 min, 45 min, 60 min, 90 min and 120 min are 1%, 2%, 6%, 11%, 14%, 21% and 29% respectively.

It can be seen from examples 20~21 that the type of disintegrating agent has a certain impact on the hardness and dissolution of the tablet, and the effect of croscarmellose sodium as disintegrating agent is the best.

Example 22: Preparation Method of Pharmaceutical Preparations

Weigh the solid dispersion prepared in example 8, microcrystalline cellulose (Avicel® PH101), croscarmellose sodium and colloidal silica (wherein the mass proportions of solid dispersion, microcrystalline cellulose (Avicel® PH101), croscarmellose sodium and colloidal silica in the total material are 66.7%, 26.3%, 5% and 2%, respectively) the solid dispersion, microcrystalline cellulose (Avicel® PH101), croscarmellose sodium and colloidal silica are sieved, crushed and mixed. The specific operation and parameters are the same as those in example 8.

The tablets were pressed on the experimental tablet press (ZP14) with a 10 mm Round die to make plain tablets with a tablet weight of 300 mg. The parameters and drug dissolution of plain tablets were tested, in which the average hardness was 26N and the average thickness was 4.85 mm. In terms of dissolution (paddle method, taking 900 ml pH 6.8 phosphate solution (0.2% sodium dodecyl sulfate) as the dissolution medium and the rotating speed is 75 rpm), the drug dissolution in 5 min, 15 min, 30 min, 45 min, 60 min, 90 min and 120 min are 3%, 14%, 38%, 58%, 73%, 89% and 96% respectively. The experimental results show that compared with example 20, the addition of 2% colloidal silica in the formula of this example has no effect on the physical and chemical properties of the tablet and promotes the dissolution of the drug.

Example 23: Preparation Method of Pharmaceutical Preparations

Weigh the solid dispersion prepared in example 8, microcrystalline cellulose (Avicel® PH102), calcium phosphate, croscarmellose sodium, colloidal silica and magnesium stearate (wherein the mass proportions of solid dispersion, microcrystalline cellulose (Avicel® PH102), calcium phosphate, croscarmellose sodium, colloidal silica and magnesium stearate in the total material are 48.9%, 14.6%, 29.3% 4.9%, 2% and 0.3% respectively), the solid dispersion, microcrystalline cellulose (Avicel® PH102), calcium phosphate, croscarmellose sodium, colloidal silica and magnesium stearate are screened, crushed and mixed. The specific operation and parameters are the same as those in example 8.

The tablet was pressed on the experimental tablet press (ZP14) with a 10 mm Round die, and a plain tablet with a tablet weight of 409.2 mg was made. The tablet pressing was normal. The parameters of plain tablets were tested, in which the average hardness was 60N, the average thickness was 5.01 mm, and the disintegration time was 4 minutes and 23 seconds.

Example 24: Preparation Method of Pharmaceutical Preparations

Weigh the solid dispersion prepared in example 8, microcrystalline cellulose (Avicel® PH102), calcium phosphate, croscarmellose sodium, colloidal silica and magnesium stearate (wherein the mass proportions of solid dispersion, microcrystalline cellulose (Avicel® PH102), calcium phosphate, croscarmellose sodium, colloidal silica and magnesium stearate in the total material are 48.8%, 14.6% and 29.2%, 4.9%, 2% and 0.5% respectively), the solid dispersion, microcrystalline cellulose (Avicel® PH102), calcium phosphate, croscarmellose sodium, colloidal silica and magnesium stearate are screened, crushed and mixed. The specific operation and parameters are the same as those in example 8.

The tablets were pressed on the experimental tablet press (ZP14) with a 10 mm Round die to make a plain tablet with a tablet weight of 410 mg. The tablet pressing was normal. The parameters of plain tablets were tested, in which the average hardness was 56N, the average thickness was 5.04 mm, and the disintegration time was 4 minutes and 40 seconds.

Example 25: Preparation Method of Pharmaceutical Preparations

Weigh the solid dispersion prepared in example 8, microcrystalline cellulose KG802, calcium phosphate, croscarmellose sodium, colloidal silica and magnesium stearate (wherein the mass proportions of solid dispersion, microcrystalline cellulose KG802, calcium phosphate, croscarmellose sodium, colloidal silica and magnesium stearate in the total material are 50%, 21%, 21%, 5%, 2% and 1%, respectively), The solid dispersion, microcrystalline cellulose KG802, calcium phosphate, croscarmellose sodium, colloidal silica and magnesium stearate are screened, crushed and mixed. The specific operation and parameters are the same as those in example 8.

The tablets were pressed on the experimental tablet press (ZP14) with a 10 mm Round die to make plain tablets with a tablet weight of 400 mg. The tablet pressing was normal. The parameters of plain tablets were tested, in which the average hardness was 64N, the average thickness was 5.25 mm, and the disintegration time was 7 minutes and 02 seconds.

Example 26: Preparation Method of Pharmaceutical Preparations

API is sensitive to light. Referring to the preparation method of example 15, gastric soluble film coating premix (Opadry® II 85F92209 yellow) for tablet coating, the target coating weight gain is 3% (that is, the coating is performed based on the plain tablets in example 15, and the resulting coated tablets contain about 3% of the coating material by the weight of the plain tablets). The results showed that in the coated tablets, the content (calculated as dry product) was 99.8%, the total impurity was 1.73%, and the dissolution (paddle method, taking 900 ml pH6.8 phosphate solution (0.2% sodium dodecyl sulfate) as the dissolution medium, and the rotating speed was 75 rpm). The dissolution in 5 min, 15 min, 30 min, 45 min, 60 min, 90 min and 120 min were 6%, 22%, 55%, 77%, 87%, 94% and 95% respectively, meet the quality requirements.

Example 27: Preparation Method of Solid Dispersion

The API and carrier PVP VA64 prepared in example 1 are mixed in a suitable hopper machine according to the proportion of drug loading of 25% (i.e. drug loading ratio of 1:3). The conventional hopper mixer is used for premixing. The hot-melt extrusion parameters are shown in Table 1 below. The resulting extrudate is a solid dispersion.

TABLE 1

| | Condition1 | Condition2 | Condition 3 | Condition 4 | Condition 5 | Condition 6 |
|---|---|---|---|---|---|---|
| Set temperature (° C.) | 180 | 185 | 185 | 185 | 200 | 195 |
| Feeding speed (g/min) | 20 | 20 | 30 | 30 | 20 | 30 |
| Appearance | transparent | transparent | transparent | transparent | transparent | transparent |
| Total impurities (%) | 1.77 | 1.89 | 1.71 | 1.77 | 2.37 | 2.08 |

The extrudates obtained at the extrusion temperature of 180~200° C. were amorphous.

Figure 3:
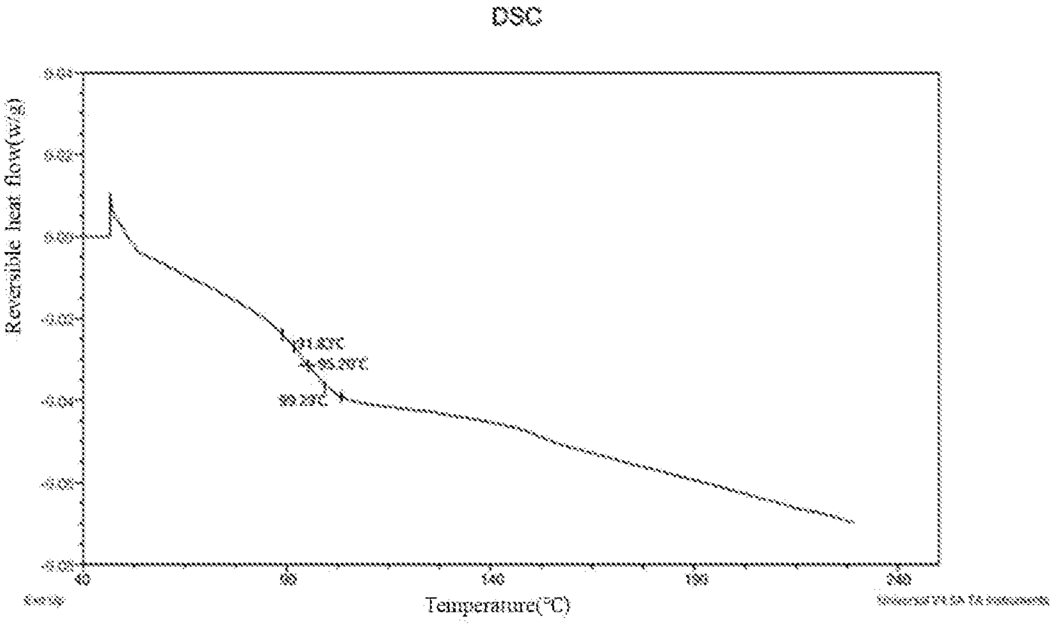
FIG. 3 shows the DSC spectrum of solid dispersion prepared under condition 3 of example 27.

The solid dispersion prepared under condition 3 is scanned by DSC. See FIG. 3. There is no characteristic peak of the crystal form of the active ingredient in the DSC spectrum. The results show that the active ingredient is dispersed in the carrier in an amorphous state.

Example 28: Preparation Method of Pharmaceutical Preparations in this Example, the Preparation is Composed of the Following Constituents The API prepared in example 1 was 12.14% (w/w),
PVP VA64 36.41% (w/w),
Microcrystalline cellulose KG802 20.39% (w/w),
Calcium phosphate 20.39% (w/w),
Croscarmellose sodium 4.85% (w/w),
Colloidal silica 1.94% (w/w),
Magnesium stearate 0.97% (w/w)
Opadry® II film coating premix 2.91% (w/w).

The solid dispersion was prepared according to the method of condition 3 of example 27, and the preparation with the specification of 50 mg was prepared according to the preparation method of example 8.

Determine the dissolution (paddle method, with 900 ml pH6.8 phosphate solution (0.2% sodium dodecyl sulfate) as the dissolution medium, rotating speed of 75 RPM), content and related substances of the preparation according to the above method, and make two batches. The analysis data are shown in Table 2:

TABLE 2

| Specifications | Batch number | Drug dissolution (%) (45 min, 75 rpm) | Single impurity | Total impurities | content |
|---|---|---|---|---|---|
| 50 mg | B1 | 100 | Maximum single impurity 0.28% | 1.3% | 100.7% |
| | B2 | 99 | Maximum single impurity 0.48% | 1.3% | 101.2% |

It can be seen from the results that the minimum dissolution of different batches of 50 mg preparation at 45 min and 75 rpm is 99%. The single impurity of different batches shall not exceed 0.5%, and the total impurity shall not exceed 1.5%. The content limit and content uniformity meet the expectations.

Example 29: Preparation Method of Pharmaceutical Preparations

In this embodiment, the preparation is composed of the following constituents:

The API prepared in example 1 was 14.8% (w/w),
PVP VA64 44.4% (w/w),
Microcrystalline cellulose KG802 13.9% (w/w),
Calcium phosphate 13.9% (w/w),
Croscarmellose sodium 10% (w/w),
Colloidal silica 2% (w/w),
Magnesium stearate 1% (w/w).

The solid dispersion was prepared according to the method of condition 3 of example 27, and the preparation with a specification of 200 mg was prepared according to the preparation method of example 8.

Determine the dissolution of the preparation according to the above method (paddle method, take 900 ml pH6.8 phosphate solution (0.5% sodium dodecyl sulfate) as the dissolution medium, and the rotating speed is 75 RPM) and related substances for two batches. The analysis data are shown in Table 3:

TABLE 3

| Specifications | Batch number | Drug dissolution (%) (45 min, 75 rpm) | Single impurity | Total impurities |
|---|---|---|---|---|
| 200 mg | C1 | 96 | Maximum single impurity 0.09% | 0.49% |
| | C2 | 94 | Maximum single impurity 0.05% | 0.34% |

It can be seen from the results that the dissolution of different batches of 200 mg preparation at 45 min and 75 rpm is greater than 90%. The single impurity of different batches shall not exceed 0.5%, and the total impurity shall not exceed 1.5%.

Example 30

The API prepared in example 1 and carrier PVP VA6 were sieved through 30 meshes respectively, added into a 50 L hopper mixer, and mixed at a mixing speed of 20 rpm for 10 minutes, in which the mass ratios of API and PVP VA6 were 12.5% and 37.5% respectively.

The above-mixed materials are added to the feeder of the hot-melt extruder and hot-melt extrusion is carried out in the hot-melt extruder. The process parameters are: operating temperature 180~200° C., screw speed 95~105 rpm and dosing speed 25~35 g/min; The extrudate obtained is a solid dispersion.

The solid dispersion, microcrystalline cellulose KG802, calcium phosphate, croscarmellose sodium, colloidal silica and magnesium stearate (in which the mass proportions of solid dispersion, microcrystalline cellulose KG802, calcium phosphate, croscarmellose sodium, colloidal silica and magnesium stearate in the total material are 50%, 21%, 21%, 5%, 2% and 1%, respectively) are sieved, crushed and mixed, the specific operation and parameters are the same as those in example 8.

The tablets were pressed on the experimental tablet press (ZP14) with a 10 mm of the plain sheet, in which the average hardness is 50N.

Example 31

Pass the API prepared in example 1, carrier PVP VA64 and colloidal silica through the 30 mesh screens respectively, mix the screened materials evenly (shake and mix in the LDPE bag for 100 times after passing the 30 mesh screens for 3 times), and then add them into the pulverizer; In the weight reduction method, the plastic dropper takes the prescribed amount of Tween 80, drops it evenly into the mixed powder, and starts the pulverizer to mix Tween 80 and the powder evenly; The mass ratio of API, carrier PVP VA64, colloidal silica and Tween 80 prepared in example 1 is 1:6.67:0.08:0.58.

The above-mixed materials are added to the feeder of the hot-melt extruder and hot-melt extrusion is carried out in the hot-melt extruder. The process parameters are: operating temperature 195° C., screw speed: 500 rpm; The extrudate obtained is a solid dispersion.

Weigh the solid dispersion, calcium hydrogen phosphate, colloidal silica and sodium stearyl fumarate (in which the mass proportions of solid dispersion, calcium hydrogen phosphate, colloidal silica and sodium stearyl fumarate in the total material are 78.49%, 20%, 1% and 0.51% respectively), the solid dispersion, calcium hydrogen phosphate, colloidal silica and sodium stearyl fumarate are sieved, crushed and mixed, the specific operation and parameters are the same as those in example 8.

The tablets were pressed on the experimental tablet press (ZP14) with a 10 mm Round die to make a plain tablet with a tablet weight of 530.9 mg. Test the parameters of the plain sheet, in which the average hardness is 120N.

Example 32: Preparation Method of Solid Dispersion

Weigh the API prepared in example 1, carrier PVP VA64 and poloxamer 188 (wherein the mass proportions of API, carrier PVP VA64 and poloxamer 188 are 19.23%, 57.69% and 23.08% respectively) through 30 mesh sieve respectively, mix the API, PVP VA64 and poloxamer 188 in the mixing barrel at a rotating speed of 20 rpm for 10 minutes, and then add them into the hot-melt extrusion hopper for hot-melt extrusion, Process parameters: 200° C.±5, screw speed: 500 rpm, the extrusion is crushed to prepare solid dispersion.

Example 33: Preparation Method of Solid Dispersion

Weigh the API prepared in example 1, carrier PVP VA64 and TPGS (wherein the mass proportions of API, carrier PVP VA64 and TPGS are 20.83%, 62.5% and 16.67% respectively) through 30 mesh sieves, mix the API, PVP VA64 and TPGS in the mixing barrel at the speed of 20 rpm for 10 minutes, and then add them into the hot-melt extrusion hopper for hot-melt extrusion. Process parameters: 200° C.±5, screw speed: 500 rpm, the prepared extrusion is crushed to obtain a solid dispersion.

Example 34: Preparation Method of Solid Dispersion

Weigh the API prepared in example 1, carrier PVP VA64 and Labrasol® (wherein the mass proportions of API, carrier PVP VA64 and Labrasol® are 22.73%, 68.18% and 9.09% respectively) through 30 mesh sieves, mix the API, PVP VA64 and Labrasol® in the mixing barrel at 20 rpm for 10 minutes, and then add them into the hot-melt extrusion hopper for hot-melt extrusion. Process parameters: 200° C.±5, Screw speed: 500 rpm, the extrusion is crushed to obtain solid dispersion.

Example 35: Preparation Method of Solid Dispersion-Carrier Type

The API prepared in example 1, HPMCAS 716G and colloidal silica were dissolved in methanol/dichloromethane (5:95, V/V) at a mass ratio of 24.5:73.5:2, and the concentration was 13.33 mg/ml. Spray drying method was used to prepare solid dispersions, and the parameters of spray drying were: pore size: 1.5 mm; Inlet air temperature: 85° C.; Air volume 100%; Peristaltic pump speed: 20-25%; Q-Flow:

20-30 mm; Peristaltic tube material: TYGON®2375, NSF-51, inner diameter: 2 mm, outer diameter: 3.7 mm.

Example 36: Preparation Method of Solid Dispersion

The API prepared in example 1, HPMCAS 716G and colloidal silica (wherein the mass proportions of API, HPMCAS 716G and colloidal silica are 12.86%, 86.14% and 1% respectively) were dissolved in methanol/dichloromethane (5:95, V/V) at a concentration of 13.33 mg/ml. Spray drying method was used to prepare solid dispersions, and the parameters of spray drying were: pore size: 1.5 mm; Inlet air temperature: 85° C.; Air volume 100%; Peristaltic pump speed: 20-25%; Q-Flow: 20-30 mm; Peristaltic tube material: TYGON®2375, NSF-51, inner diameter: 2 mm, outer diameter: 3.7 mm.

Example 37: Preparation Method of Solid Dispersion

The API, HPMCAS 716G, Tween 80 and colloidal silica prepared in example 1 (wherein the mass proportions of API, HPMCAS 716G, Tween 80 and colloidal silica are 23.3%, 69.7%, 5% and 2% respectively) were dissolved in methanol/dichloromethane (5:95, V/V) with a concentration of 13.33 mg/ml. Spray drying method was used to prepare solid dispersions, and the parameters of spray drying were: pore size: 1.5 mm; Inlet air temperature: 85° C.; Air volume 100%; Peristaltic pump speed: 20-25%; Q-Flow: 20-30 mm; Peristaltic tube material: TYGON®2375, NSF-51, inner diameter: 2 mm, outer diameter: 3.7 mm.

Example 38: Preparation Method of Solid Dispersion

The API prepared in example 1, HPMCAS 716G, and colloidal silica (wherein the mass proportions of API, HPMCAS 716G, and colloidal silica are 24.5%, 73.5%, and 2%, respectively) were dissolved in methanol/dichloromethane (5:95, V/V) at a concentration of 13.33 mg/ml. Spray drying method was used to prepare solid dispersions, and the parameters of spray drying were: pore size: 1.5 mm; Inlet air temperature: 85° C.; Air volume 100%; Peristaltic pump speed: 20-25%; Q-Flow: 20-30 mm; Peristaltic tube material: TYGON®2375, NSF-51, inner diameter: 2 mm, outer diameter: 3.7 mm.

In terms of dissolution (paddle method, taking 900 ml of pH7.4 phosphate solution (0.05% sodium dodecyl sulfate) as the dissolution medium and rotating speed of 75 revolutions per minute), the dissolution in 30 min, 60 min, 90 min, 120 min, 150 min and 180 min were 81.8%, 86.6%, 89.3%, 90.0%, 90.3% and 90.8% respectively.

Example 39: Preparation Method of Solid Dispersion

The carrier in example 38 was replaced with HPMCAS 126G, and other parameters remained unchanged. The dissolution of the solid dispersion at 30 min, 60 min, 90 min, 120 min, 150 min and 180 min were 80.9%, 87.6%, 90.3%, 90.7%, 91.0% and 91.2% respectively.

The carrier in example 38 was replaced with HPMCAS 912G, and the other parameters remained unchanged. The dissolution of the solid dispersion at 30 min, 60 min, 90 min, 120 min, 150 min and 180 min were 78.8%, 84.8%, 86.6%, 87.2%, 87.3 and 88.1% respectively.

Example 40: Preparation Method of Pharmaceutical Preparations

Weigh the solid dispersion prepared in example 36, croscarmellose sodium, calcium hydrogen phosphate, colloidal silica and sodium stearyl fumarate (wherein the mass proportions of solid dispersion, croscarmellose sodium, calcium hydrogen phosphate, colloidal silica and sodium stearyl fumarate in the total material are 70.6%, 10.0%, 18.0%, 0.9% and 0.5%, respectively), the solid dispersion, croscarmellose sodium, calcium hydrogen phosphate, colloidal silica and sodium stearyl fumarate are sieved, crushed and mixed. The specific operation and parameters are the same as those in example 8.

The tablets were pressed on the experimental tablet press (ZP14) with a 10 mm Round die to make a plain tablet with a tablet weight of 550.4 mg. The parameters of plain tablets were tested, in which the average hardness was 226N and the disintegration time was 1 minute and 30 seconds. In terms of dissolution (paddle method, taking 900 ml of pH7.4 phosphate solution (0.05% sodium dodecyl sulfate) as the dissolution medium and the rotating speed is 75 revolutions per minute), the dissolution in 30 min and 60 min are 43.5% and 91.4% respectively.

Example 41: Preparation Method of Formulation

Weigh the solid dispersion prepared in example 37, microcrystalline cellulose, croscarmellose sodium, calcium phosphate, colloidal silica and magnesium stearate (wherein the mass proportions of solid dispersion, microcrystalline cellulose, croscarmellose sodium, calcium phosphate, colloidal silica and magnesium stearate in the total material are 53.7%, 19.2%, 5.0%, 19.2%, 2.0% and 1.0%, respectively), the solid dispersion, microcrystalline cellulose, croscarmellose sodium, calcium phosphate, colloidal silica and magnesium stearate are screened, crushed and mixed. The specific operation and parameters were the same as those in example 8.

The tablets were pressed on the experimental tablet press (ZP14) with a 10 mm Round die to make a plain tablet with a tablet weight of 400 mg. The parameters of plain tablets were tested, in which the average hardness was 100.4N and the disintegration time was 23 seconds. In terms of dissolution (paddle method, taking 900 ml pH6.8 phosphate solution (0.2% sodium dodecyl sulfate) as the dissolution medium and the rotating speed is 75 rpm), the dissolution in 5 min, 15 min, 30 min, 45 min and 60 min are 96.6%, 99.7%, 98.4%, 98.8% and 100.2% respectively.

Example 42: Preparation Method of Solid Dispersion-Hot-Melt Extrusion

Weigh the API prepared in example 1, HPMCAS 716G and TPGS (wherein the mass proportions of API, HPMCAS 716G and TPGS are 30%, 60% and 10% respectively) through 30 mesh sieve, mix the API, HPMCAS 716G and TPGS at the speed of 20 rpm in the mixing barrel for 10 minutes, and then add them into the hot-melt extrusion hopper for hot-melt extrusion. Process parameters: 180° C., feed speed: 30 rpm, Screw speed: 100 rpm, the extrusion is crushed to obtain solid dispersion.

Case 43: Preparation Method of Solid Dispersion-Spray Drying

Weigh the API prepared in example 1, HPMCAS 716G and TPGS (wherein the mass proportions of API, HPMCAS 716G and TPGS are 30%, 60% and 10% respectively) and dissolve them in methanol/dichloromethane (5:95, V/V) with a concentration of 13.33 mg/ml. Spray drying method was used to prepare solid dispersions, and the parameters of spray drying were: pore size: 1.5 mm; Inlet air temperature: 85° C.; Air volume 100%; Peristaltic pump speed: 20-25%; Q-Flow: 20-30 mm; Peristaltic tube material: TYGON®2375, NSF-51, inner diameter: 2 mm, outer diameter: 3.7 mm.

Example 44: Preparation Method of Solid Dispersion

The acetone solvates of the compound of formula (I) and the carrier PVP VA64 of example 2 were respectively passed through a 30 mesh screens, added into the hopper mixer according to the proportion of drug loading of 25% (i.e. drug loading ratio of 1:3), mixed for 10 minutes at the mixing speed of 20 rpm, and hot-melt extrusion was carried out in a hot-melt extruder. The process parameters were: operating temperature 165° C., screw speed: 150 rpm; The extrudate obtained is a solid dispersion.

In terms of dissolution (paddle method, taking 900 ml of pH6.8 phosphate solution (0.2% sodium dodecyl sulfate) as the dissolution medium and the rotating speed is 75 rpm), the drug dissolution in 5 min, 15 min, 30 min, 45 min, 60 min and 90 min are 57.6%, 88.4%, 97.9%, 99.7%, 99.9% and 100.0% respectively.

Figure 4:
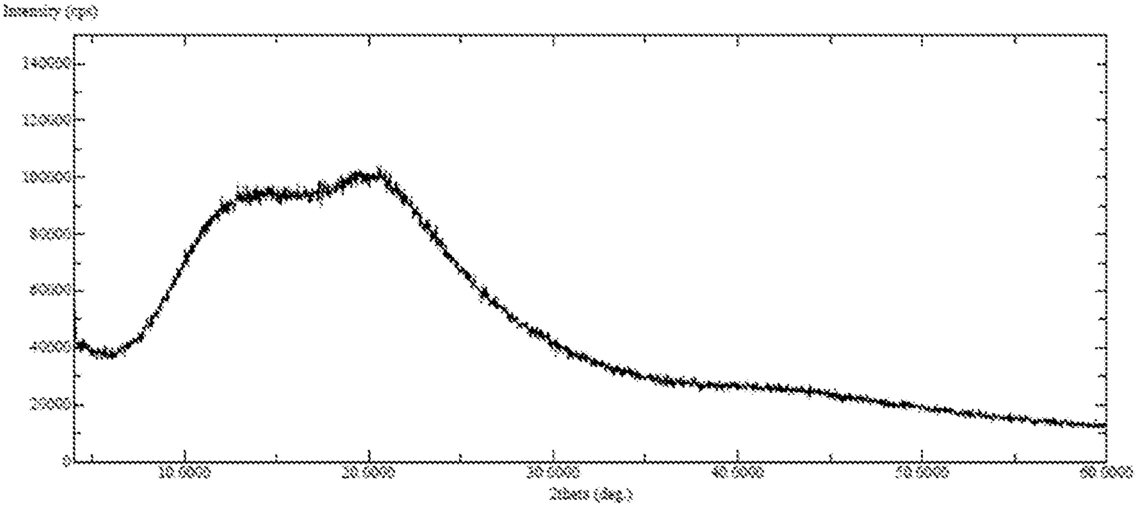
FIG. 4 shows the XRD pattern of solid dispersion of example 44.

The prepared solid dispersion was detected by XRD. The results are shown in FIG. 4. There is no characteristic peak of the crystal form of the active ingredient in the XRD spectrum. The results show that the active ingredient is dispersed in the carrier in an amorphous state.

Example 45: Preparation Method of Solid Dispersion

The acetonitrile solvates of the compound of formula (I) of example 3 and the carrier PVP VA64 are respectively passed through a 30 mesh screens, added into the hopper mixer according to the proportion of drug loading of 25% (i.e. drug loading ratio of 1:3), mixed at the mixing speed of 20 rpm for 10 minutes, and hot-melt extrusion is carried out in a hot-melt extruder. The process parameters are: operating temperature 165° C., screw speed: 150 rpm; The extrudate obtained is a solid dispersion.

In terms of dissolution (paddle method, taking 900 ml pH6.8 phosphate solution (0.2% sodium dodecyl sulfate) as the dissolution medium and the rotating speed is 75 rpm), the drug dissolution in 5 min, 15 min, 30 min, 45 min, 60 min and 90 min are 57.9%, 89.3%, 97.9%, 99.6%, 99.7% and 100.0% respectively.

Figure 5:
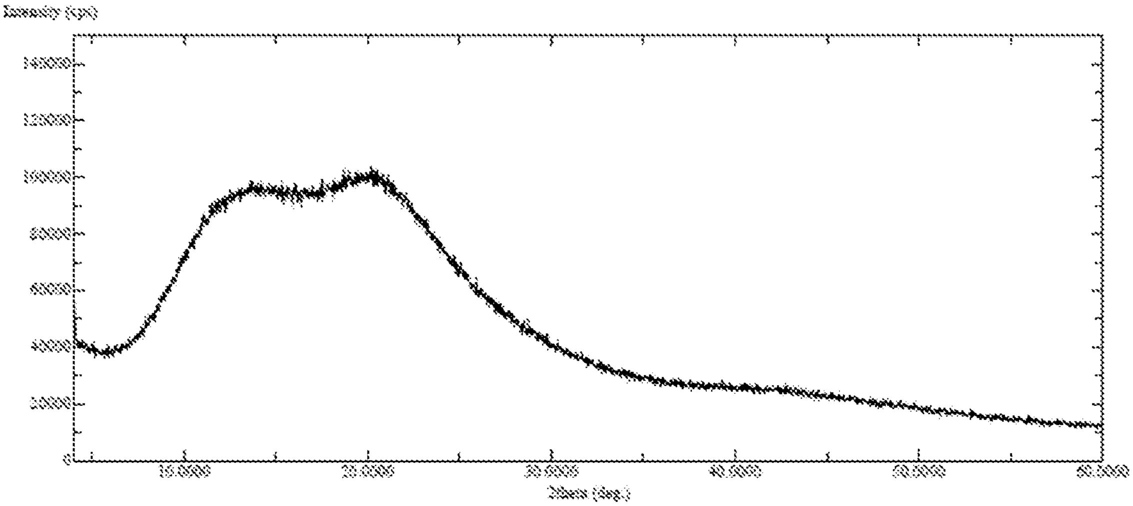
FIG. 5 shows the XRD pattern of the solid dispersion of example 45.

The prepared solid dispersion was detected by XRD. The results are shown in FIG. 5. There is no characteristic peak of the crystal form of the active ingredient in the XRD spectrum. The results show that the active ingredient is dispersed in the carrier in an amorphous state.

Effect Example 1: Equilibrium Solubility Test

Determination of equilibrium solubility: the excess API (prepared in example 1) and solid dispersion were mixed with the solvent at 37° C. and stirred for 2 and 24 hours respectively. After 2 and 24 hours of high-speed centrifugation, the supernatant was taken, and the concentration of API in the supernatant was determined by high-performance liquid chromatography. The determination results of equilibrium solubility of API in different solvents are shown in Table 4 below:

TABLE 4

| Menstruum | Time | 37° C., solubility(mg/mL) API | Solid dispersion prepared under condition 3 of Example 27 (API: PVP VA64 = 1:3) |
|---|---|---|---|
| FaSSIF | 2 h | 0.0013 | 0.1562 |
| | 24 h | 0.0006 | 0.0168 |
| FeSSIF | 2 h | 0.0025 | 0.0987 |
| | 24 h | 0.0005 | 0.0094 |

It can be seen from the above results that the equilibrium solubility is greatly improved after API is prepared as a solid dispersion.

Effect Example 2: Bioavailability Test

Test Conditions for Absolute Bioavailability in Mice:

Oral gavage group: 72 CD-1 mice (half male and half female) were randomly divided into three groups, 12/sex/group. The test article (solid dispersion prepared in Example 7) was administered by gavage at the dosage of 25, 50 and 100 mg/kg, and the solvent was reverse osmosis (R.O.) water.

Intravenous administration group: 24 CD-1 mice, half male and half female, were given the test article (API prepared in example 1) by single intravenous injection. The dosage was 2 mg/kg, and the solvent was 5% DMSO+5% Solutol HS15+90% normal saline.

Blood samples were collected from all animals before administration and 0.083 h (intravenous injection only), 0.25 h, 0.5 h, 1 h, 2 h, 4 h, 6 h, 8 h, 12 h and 24 h after administration. The validated LC-MS/MS analysis method was used to detect the drug concentration in plasma. The lower limit of quantification of the analysis method was 2 ng/ml. The non atrioventricular model (NCA) of winnonlin was used to analyze the plasma concentration data and calculate the pharmacokinetic parameters.

Beagle Absolute Bioavailability Test Conditions:

Three female and three male beagle dogs were selected and divided into oral test articles (solid dispersion suspension prepared in Example 7) group, with three doses of 5, 10 and 20 mg/kg respectively, and intravenous test article (API solution prepared in example 1) group, with the dosage of 0.5 mg/kg. The solvent of oral gavage group was reverse osmosis (R.O.) water, and that of intravenous injection group was 5% DMSO+5% Solutol HS15+90% normal saline.

Blood samples were collected before administration and 0.083 h (intravenous injection only), 0.25 h, 0.5 h, 1.0 h, 2.0 h, 4.0 h, 6.0 h, 8.0 h, 24 h, 48 h and 72 h after administration. The validated LC-MS/MS method was used to detect the drug concentration in dog plasma. The lower limit of quantification of the method was 2 ng/ml. The non atrioventricular model (NCA) of winnonlin was used to analyze the plasma concentration data, calculate the pharmacokinetic parameters, and calculate the absolute bioavailability.

As described above, using the solid dispersion prepared in Example 7, two animal models of mice and beagle dogs were selected for pharmacokinetic behavior evaluation. The results showed that the absolute bioavailability of the solid dispersion in mice and dogs were 19%~27.2% and 19.5%~23.6% respectively.

Effect Example 3: Pharmacokinetic Test

Four groups of male mice were randomly divided into two groups: test article 1 (solid dispersion prepared in Example 7 and suspension prepared with reverse osmosis water as solvent), the dosages are 25 mg/kg and 100 mg/kg respectively; test article 2 (API prepared in example 1 and suspension prepared with aqueous solution containing 0.2% HPMC-E5), the dosages are 25 mg/kg and 100 mg/kg, respectively. The animals in each group were administered by single gavage.

All animals collected blood samples and separated plasma at 0.087 h, 0.25 h, 0.5 h, 1 h, 2 h, 4 h, 6 h, 8 h and 24 h after administration. All plasma samples were analyzed by LC-MS/Ms. the lower limit of quantification of the method was 10 ng/ml. The plasma concentration data were analyzed by non-compartmental model method (NCA) of metabolic kinetic data analysis software winnonlin8.0.0.3176, and the pharmacokinetic parameters were calculated to evaluate the kinetic characteristics of API in animals after administration. The results are shown in Table 5.

TABLE 5

| Sample | Dosage (mg/kg) | Tmax (hr) | Cmax (ng/mL) | $T_{1/2}$ (hr) | $AUC_{0\text{-}last}$ (hr*ng/mL) | $AUC_{0\text{-}\infty}$ (hr*ng/mL) |
|---|---|---|---|---|---|---|
| Solid dispersion | 25 | 4.00 | 2880 | 1.87 | 21200 | 21200 |
| prepared in Example 7 | 100 | 4.00 | 11700 | 2.15 | 120000 | 120000 |
| API prepared | 25 | 3.33 | 82.2 | 7.41 | 384 | 637 |
| in example 1 | 100 | 1.00 | 105 | 3.7 | 1101 | 1115 |

Effect Example 4: Long Term Stability Test

A long-term stability study was conducted on the preparation with the specification of 50 mg and batch No. B1 in example 28. The sample was placed at 40±2° C. and 75%±5% RH for 6 months. The results are shown in Table 6.

TABLE 6

| Investigation items | Time (month) 0 | 1 | 2 | 3 | 6 |
|---|---|---|---|---|---|
| Appearance | This product is a light yellow, round biconvex light arc film coated tablet | This product is a light yellow, round biconvex light arc film coated tablet | This product is a light yellow, round biconvex light arc film coated tablet | This product is a light yellow, round biconvex light arc film coated tablet | This product is a light yellow, round biconvex light arc film coated tablet |
| Water content | 2.9% | 2.8% | 3.2% | 3.0% | 3.5% |
| Dissolution | 100% | 93% | 95% | 94% | 99% |
| Related substances | 1.3% | 1.4% | 1.4% | 1.2% | 1.6% |
| Content determination | 100.7% | 100.4% | 98.4% | 99.2% | 96.5% |

The above results show that there is no significant change in each test item.

Effect Example 5: Pharmacokinetic Test-Beagle Dog

Three male beagle dogs were selected and divided into oral test articles (uncoated tablets) group. The dosage was 5 mg/kg, and the solvent was purified water.

Blood samples were collected at 1.0 h, 2.0 h, 4.0 h, 6.0 h, 8.0 h, 24 h and 48 h after administration. The validated LC-MS/MS method was used to detect the drug concentration in dog plasma. The lower limit of quantification of the method was 2 ng/ml. The non atrioventricular model (NCA) of winnonlin was used to analyze the plasma concentration data and calculate the pharmacokinetic parameters.

The results are shown in Table 7.

TABLE 7

| Pharmacokinetic parameters of Beagle Dogs | | | | | | |
|---|---|---|---|---|---|---|
| Sample | Dosage (mg/kg) | Tmax (hr) | Cmax (ng/mL) | $T_{1/2}$ (hr) | $AUC_{0\text{-}last}$ (hr*ng/mL) | $AUC_{0\text{-}\infty}$ (hr*ng/mL) |
| Tablet prepared in example 30 | 5 | 3.33 | 1246 | 8.42 | 13775 | 14069 |

Effect Example 6: Pharmacokinetic Test-Mice

Nine male CD-I mice were randomly selected. The test sample was solid dispersion, and the suspension was prepared with purified water as solvent. The dosage was 50 mg/kg. All animals were administered by single gavage.

All animals collected blood samples and separated plasma at 0.083 h, 0.25 h, 0.5 h, 1 h, 2 h, 4 h, 6 h, 8 h and 24 h after administration. All plasma samples were analyzed by LC-MS/Ms. the lower limit of quantification of the method was 10 ng/ml. The plasma concentration data were analyzed by non-compartmental model method (NCA) of metabolic kinetic data analysis software winnonlin8.0.0.3176, and the pharmacokinetic parameters were calculated to evaluate the kinetic characteristics of API in animals after administration. The results are shown in Table 8.

TABLE 8

| Pharmacokinetic parameters of mice | | | | | | |
|---|---|---|---|---|---|---|
| Sample | Dosage (mg/kg) | Tmax (hr) | Cmax (ng/mL) | $T_{1/2}$ (hr) | $AUC_{0\text{-}last}$ (hr*ng/mL) | $AUC_{0\text{-}\infty}$ (hr*ng/mL) |
| Solid dispersion prepared in example 34 | 50 | 4.00 | 5097 | 2.25 | 65268 | 65339 |

Effect Example 7: Pharmacokinetic Test-Mice

Oral gavage group: 9 CD-1 mice were selected, and the test substance (solid dispersion) was given by gavage for a single time. The dosage was 50 mg/kg, and the solvent was purified water.

Blood samples were collected at 0.083 h, 0.25 h, 0.5 h, 1 h, 2 h, 4 h, 6 h, 8 h and 24 h after administration. The validated LC-MS/MS analysis method was used to detect the drug concentration in plasma. The lower limit of quantification of the analysis method was 10 ng/ml. The non-compartmental model (NCA) of winnonlin was used to analyze the plasma concentration data, calculate the pharmacokinetic parameters, and evaluate the kinetic characteristics of API in animals after administration. The results are shown in Table 9.

TABLE 9

| pharmacokinetic parameters of mice | | | | | | |
|---|---|---|---|---|---|---|
| Sample | Dosage (mg/kg) | Tmax (hr) | Cmax (ng/mL) | $T_{1/2}$ (hr) | $AUC_{0\text{-}last}$ (hr*ng/mL) | $AUC_{0\text{-}\infty}$ (hr*ng/mL) |
| Solid dispersion prepared in example 37 | 50 | 2.00 | 6263 | 2.21 | 52678 | 52723 |

Effect Example 8: Pharmacokinetic Test-Beagle Dog

Three male beagle dogs were selected for this test. The test substance (solid dispersion suspension) was orally administered at the dosage of 5 mg/kg.

Blood samples were collected before administration and 0.083 h, 0.25 h, 0.5 h, 1.0 h, 2.0 h, 4.0 h, 6.0 h, 8.0 h, 24 h and 48 h after administration. The validated LC-MS/MS method was used to detect the drug concentration in dog plasma. The lower limit of quantification of the method was 2 ng/ml. The non atrioventricular model (NCA) of winnonlin was used to analyze the plasma concentration data and calculate the pharmacokinetic parameters. The results are shown in Table 10.

TABLE 10

| Sample | Dosage (mg/kg) | Tmax (hr) | Cmax (ng/mL) | $T_{1/2}$ (hr) | $AUC_{0-last}$ (hr*ng/mL) | $AUC_{0-\infty}$ (hr*ng/mL) |
|---|---|---|---|---|---|---|
| Tablet prepared in example 42 | 5 | 4.00 | 1890 | 8.64 | 26266 | 26885 |

The invention claimed is:

1. A solid dispersion, comprising:

an active ingredient which is a compound as shown in formula (I), (I)

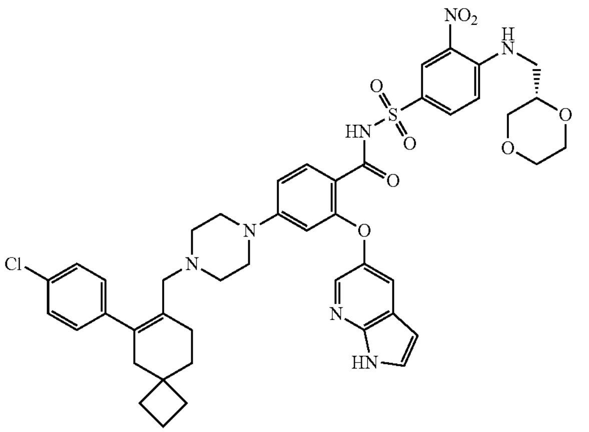

a pharmaceutically acceptable salt thereof, or a solvate thereof; and a carrier, wherein the carrier is a copolymer of povidone (PVP) and polyvinyl acetate; and the solid dispersion comprises 1 part of the active ingredient and between 1 and 10 parts of the carrier.

2. The solid dispersion according to claim 1, wherein, the carrier is copolymer of 1-vinyl-2-pyrrolidone and vinyl acetate in a ratio of 6:4 by mass (PVP VA64);

the solid dispersion further comprises a surfactant, wherein the surfactant is one or more selected from the group consisting of caprylocaproyl macrogolglycerides, tocopherol polyethylene glycol succinate (TPGS), poloxamer and polysorbate 80;

the mass ratio of the surfactant to the active ingredient is from a ratio of 0.1:1 to 5:1;

the solid dispersion further comprises a glidant, wherein the glidant is colloidal silica; and the mass ratio of the glidant to the active ingredient is from a ratio of 0.02:1 to 1:1.

3. The solid dispersion according to claim 1, wherein, the solid dispersion comprises:

1 part of the active ingredient, from 1 to 10 parts of the carrier and from 0.1 to 5 parts of a surfactant;

1 part of the active ingredient, from 1 to 10 parts of the carrier and from 0.02 to 1 part of a glidant; or 1 part of the active ingredient, from 1.5 to 7 parts of the carrier, from 0.1 to 5 parts of surfactant and from 0.02 to 0.2 parts of glidant.

4. The solid dispersion according to claim 1, wherein, the solid dispersion comprises 1 part of the active ingredient and 4 parts of copolymer of 1-vinyl-2-pyrrolidone and vinyl acetate in a ratio of 6:4 by mass (PVP VA64);

1 part of the active ingredient and 3 parts of PVP VA64;

1 part of the active ingredient, 6.7 parts of PVP VA64, 0.58 parts of polysorbate 80 and 0.0834 parts of colloidal silica;

1 part of the active ingredient, 3 parts of PVP VA64 and 1.2 parts of poloxamer;

1 part of the active ingredient, 3 parts of PVP VA64 and 0.8 parts of TPGS; or 1 part of the active ingredient, 3 parts of PVP VA64 and 0.4 parts of caprylocaproyl macrogolglycerides.

5. A method for preparing the solid dispersion of claim 1, wherein, the method comprises:

mixing one or more selected from the group consisting of the compound of formula I, its pharmaceutically acceptable salt and its solvate, and other constituents with a solvent to form a solution or suspension; and removing the solvent to obtain the solid dispersion.

6. The method of claim 5, wherein, the solvent is one or more selected from the group consisting of water, alcohol solvent, ester solvent, ketone solvent, halohydrocarbon solvent, nitrile solvent and ether solvent; and the mass to volume ratio of one or more selected from the group consisting of the compound of formula I and its pharmaceutically acceptable salt to the solvent is from a ratio of 0.1:1 mg/ml to 30:1 mg/ml.

7. The dispersion of claim 1, further comprising one or more selected from the group consisting of a filler and a disintegrating agent.

8. The dispersion according to claim 7, wherein, the filler is one or more selected from the group consisting of microcrystalline cellulose, lactose, pregelatinized starch, calcium hydrogen phosphate and calcium phosphate;

wherein the mass of the solid dispersion of claim 1 is 1 part and the mass part number of the filler is from 0.2 to 8 parts;

the disintegrating agent is one or more selected from the group consisting of croscarmellose sodium, low-substituted sodium hydroxypropyl cellulose and carboxymethyl starch sodium;

wherein the mass part number of the solid dispersion of claim 1 is 1 part and the mass part number of the disintegrating agent is from 0.03 to 0.4 parts; and wherein the solid dispersion further comprises one or more selected from the group consisting of glidant, lubricant, and coating material.

9. The dispersion according to claim 8, wherein, the filler is a combination of microcrystalline cellulose and calcium phosphate and the mass ratio of the solid dispersion of claim 1 to the combination of microcrystalline cellulose and calcium phosphate is from a ratio of 1:0.5 to 1:2.

10. The dispersion according to claim 7, wherein, the dispersion comprises:

1 part of the solid dispersion of claim 1, from 0.2 to 8 parts of the filler and from 0.03 to 0.4 parts of the disintegrating agent;

1 part of the solid dispersion of claim 1, from 0.2 to 8 parts of the filler, from 0.03 to 0.4 parts of the disintegrating agent and from 0.006 to 0.2 parts of a glidant;

1 part of the solid dispersion of claim 1, from 0.2 to 8 parts of the filler, from 0.03 to 0.4 parts of the disintegrating agent, from 0.006 to 0.2 parts of the glidant and from 0.004 to 0.1 parts of a lubricant; or 1 part of the solid dispersion of claim 1, from 0.2 to 8 parts of the filler, from 0.03 to 0.4 parts of the disintegrating agent, from 0.006 to 0.2 parts of the glidant, from 0.004 to 0.1 parts of the lubricant and from 0.01 to 0.2 parts of a coating agent.

11. The dispersion according to claim 1, wherein, the dispersion is further characterized as:

1 part of the solid dispersion of claim 1 and 0.05 part of colloidal silica;

1 part of the solid dispersion of claim 1 and 0.9 part of microcrystalline cellulose PH102 and 0.1 parts of croscarmellose sodium;

1 part of the solid dispersion of claim 1 and 0.6 part of microcrystalline cellulose PH102, 0.3 parts lactose and 0.1 parts croscarmellose sodium;

1 part of the solid dispersion of claim 1 and 0.6 part of microcrystalline cellulose PH102, 0.3 parts of pregelatinized starch and 0.1 parts of croscarmellose sodium;

1 part of the solid dispersion of claim 1 and 0.6 part of microcrystalline cellulose PH102, 0.3 parts of calcium phosphate and 0.1 parts of croscarmellose sodium;

1 part of the solid dispersion of claim 1 and 0.45 part of microcrystalline cellulose PH102, 0.45 parts of calcium phosphate and 0.1 parts of croscarmellose sodium;

1 part of the solid dispersion of claim 1 and 0.3 part of microcrystalline cellulose PH102, 0.6 parts of calcium phosphate and 0.1 parts of croscarmellose sodium;

1 part of the solid dispersion of claim 1 and 0.428 part of microcrystalline cellulose PH102, 0.428 parts of calcium phosphate, 0.1 parts of croscarmellose sodium, 0.04 parts of colloidal silica and 0.06 parts of magnesium stearate;

1 part of the solid dispersion of claim 1, 0.45 part of silicified microcrystalline cellulose 90, 0.45 part of calcium phosphate and 0.1 part of croscarmellose sodium;

1 part of the solid dispersion claim 1, 0.45 part of silicified microcrystalline cellulose HD 90, 0.45 part of calcium phosphate and 0.1 part of croscarmellose sodium;

1 part of the solid dispersion of claim 1, 0.43 part of microcrystalline cellulose PH105, 0.43 part of calcium phosphate, 0.1 part of croscarmellose sodium and 0.04 part of colloidal silica;

I part of the solid dispersion of claim 1, 0.43 part of microcrystalline cellulose KG802, 0.43 part of calcium phosphate, 0.1 part of croscarmellose sodium and 0.04 part of colloidal silica;

1 part of the solid dispersion of claim 1 and 0.42 part of microcrystalline cellulose PH101 and 0.07 parts of croscarmellose sodium;

1 part of the solid dispersion of claim 1 and 0.42 part of microcrystalline cellulose PH101 and 0.07 parts of low-substituted hydroxypropyl cellulose sodium;

1 part of the solid dispersion of claim 1 and 0.39 part of microcrystalline cellulose PH101, 0.07 parts of croscarmellose sodium and 0.03 parts of colloidal silica;

1 part of the solid dispersion of claim 1 and 0.3 part of microcrystalline cellulose PH102, 0.6 parts of calcium phosphate, 0.1 parts of croscarmellose sodium and 0.06 parts of colloidal silica;

1 part of the solid dispersion of claim Land 0.3 part of microcrystalline cellulose PH102, 0.6 parts of calcium phosphate, 0.1 parts of croscarmellose sodium, 0.04 parts of colloidal silica and 0.01 parts of magnesium stearate;

1 part of the solid dispersion of claim 1, 0.42 part of microcrystalline cellulose KG802, 0.42 part of calcium phosphate, 0.1 part of croscarmellose sodium, 0.04 part of colloidal silica and 0.02 part of magnesium stearate;

1 part of the solid dispersion of claim 1 and 0.43 part of microcrystalline cellulose PH102, 0.43 parts of calcium phosphate, 0.1 parts of croscarmellose sodium, 0.04 parts of colloidal silica, 0.02 parts of magnesium stearate and 0.006 parts of gastric soluble film coating premix;

1 part of the solid dispersion of claim 1, 0.42 part of microcrystalline cellulose KG802, 0.42 part of calcium phosphate, 0.1 part of croscarmellose sodium, 0.04 part of colloidal silica, 0.02 part of magnesium stearate and 0.06 part of gastric soluble film coating premix;

1 part of the solid dispersion of claim 1, 0.26 part of calcium hydrogen phosphate, 0.01 part of colloidal silica and 0.006 part of sodium stearyl fumarate;

1 part of the solid dispersion of claim 1, 0.26 part of calcium hydrogen phosphate, 0.1 part of croscarmellose sodium, 0.01 part of colloidal silica and 0.007 part of sodium stearyl fumarate; or 1 part of the solid dispersion of claim 1, 0.36 part of microcrystalline cellulose, 0.36 part of calcium phosphate, 0.1 part of croscarmellose sodium, 0.04 part of colloidal silica and 0.02 part of magnesium stearate.

12. A method of treating a hyperproliferative disease, comprising administering the dispersion of claim 7 to a patient in need thereof.

13. The method of claim 12, wherein, the hyperproliferative disease is a cancer selected from acute monocytic leukemia, acute myelogenous leukemia, chronic myelogenous leukemia, chronic lymphocytic leukemia, mixed lineage leukemia, NUT-midline cancer, multiple myeloma, small cell lung cancer, neuroblastoma, lymphoma, cervical cancer, esophageal cancer, ovarian cancer, colorectal cancer, prostate cancer, and breast cancer.

14. The solid dispersion according to claim 1, wherein, the solid dispersion is an amorphous solid dispersion.

15. A method for preparing the solid dispersion of claim 1, wherein, the method comprises mixing one or more selected from the group consisting of the compound of formula I and its pharmaceutically acceptable salt, heating, and extruding to obtain the solid dispersion.

16. A method for preparing the solid dispersion of claim 1, wherein, the method comprises mixing one or more selected from the group consisting of the compound of formula I and its pharmaceutically acceptable salt, mixing with the solvent, and spray drying to obtain the solid dispersion.

* * * * *